(12) United States Patent
Holter

(10) Patent No.: US 7,090,664 B2
(45) Date of Patent: Aug. 15, 2006

(54) OSTOMY TOOLS, AND SYSTEMS AND PROCESSES FOR THEIR USE

(76) Inventor: Dwight Jerome Holter, 1472 Murex Dr., Naples, FL (US) 34102

( * ) Notice: Subject to any disclaimer, the term of this patent is extended or adjusted under 35 U.S.C. 154(b) by 252 days.

(21) Appl. No.: 10/677,816

(22) Filed: Oct. 2, 2003

(65) Prior Publication Data

US 2005/0075616 A1    Apr. 7, 2005

(51) Int. Cl.
*A61F 5/44* (2006.01)

(52) U.S. Cl. ...................................... 604/332

(58) Field of Classification Search ............... 604/277, 604/327, 332–345, 355; 55/361–382
See application file for complete search history.

(56) References Cited

U.S. PATENT DOCUMENTS

| | | | |
|---|---|---|---|
| 2,054,535 A | 9/1936 | Diack | |
| 2,667,167 A * | 1/1954 | Raiche | 604/339 |
| 3,055,368 A | 9/1962 | Baxter | |
| 3,690,320 A | 9/1972 | Riely | |
| 3,759,260 A | 9/1973 | Nolan et al. | |
| 3,908,656 A * | 9/1975 | Binard | 604/323 |
| 3,972,727 A | 8/1976 | Cohn | |
| 4,084,590 A | 4/1978 | Caraway | |
| 4,211,224 A | 7/1980 | Kubach et al. | |
| 4,274,848 A | 6/1981 | LaGro | |
| 4,296,749 A * | 10/1981 | Pontifex | 604/344 |
| 4,367,742 A | 1/1983 | Ornstein | |
| 4,411,649 A | 10/1983 | Jensen et al. | |
| 4,451,258 A | 5/1984 | Jensen | |
| 4,457,758 A * | 7/1984 | Norton | 604/324 |
| 4,479,818 A | 10/1984 | Briggs et al. | |
| 4,490,145 A | 12/1984 | Campbell | |
| 4,512,771 A * | 4/1985 | Norton | 604/324 |
| 4,579,658 A * | 4/1986 | Moller | 210/483 |
| 4,654,037 A * | 3/1987 | Fenton | 604/334 |
| 4,810,250 A * | 3/1989 | Ellenberg et al. | 604/277 |
| 4,863,447 A | 9/1989 | Smith | |
| 4,911,699 A * | 3/1990 | Fenton | 604/333 |
| 4,986,824 A | 1/1991 | Steer | |
| 5,250,042 A | 10/1993 | Torgalker et al. | |
| 5,401,264 A | 3/1995 | Leise | |
| 5,470,325 A | 11/1995 | Fundock | |
| 5,643,234 A | 7/1997 | Losko et al. | |
| 5,658,266 A * | 8/1997 | Colacello et al. | 604/333 |
| 5,658,267 A | 8/1997 | Colacello et al. | |
| 5,683,372 A * | 11/1997 | Colacello et al. | 604/333 |
| 5,728,080 A * | 3/1998 | Suyama | 604/333 |
| 5,840,073 A * | 11/1998 | Olsen | 604/333 |
| 6,007,525 A * | 12/1999 | Martell | 604/333 |
| 6,050,983 A * | 4/2000 | Moore et al. | 604/333 |
| 6,135,986 A | 10/2000 | Leisner et al. | |

(Continued)

FOREIGN PATENT DOCUMENTS

DE    36 08 933 A1 * 10/1987

*Primary Examiner*—Tatyana Zalukaeva
*Assistant Examiner*—M. G. Bogart

(57) ABSTRACT

Waste management for people with an ostomy (ostomists), and who therefore find it necessary to wear an ostomy bag, is accomplished simply through processes, systems and ostomy tools involving versatile latent tubes. Such tools include ostomy bags, filters, connectors and conveyance vessels. The tools are particularly helpful, for example, in controlling the location and disposition of ostomy wastes (and their odors) when the ostomist performs challenging routine to unusual tasks associated with ostomy care and maintenance. The tools also help to instill confidence in the users' ability to carry on normal daily business and social activities without creating embarrassment or discomfort for themselves or others.

17 Claims, 11 Drawing Sheets

U.S. PATENT DOCUMENTS

| | | |
|---|---|---|
| 6,165,159 A | 12/2000 | Blauton |
| 6,241,712 B1 * | 6/2001 | Steer .................. 604/333 |
| 6,328,719 B1 | 12/2001 | Holtermann et al. |
| 6,918,898 B1 * | 7/2005 | King .................. 604/334 |

* cited by examiner

OSTOMY TOOLS, AND SYSTEMS AND PROCESSES FOR THEIR USE

BACKGROUND OF THE INVENTION

1. Field of the Invention

The present invention relates to systems, processes and tools for management of human body solid, liquid and gaseous wastes, including collection bags and other tools used for minimizing personal negatives for people who must use collection bags of the kind having an inlet aperture for connection of the bag directly or indirectly to a person's skin surrounding a surgically established waste outlet commonly referred to as a stoma.

2. Background Art

A stoma, an outlet through the abdominal wall, is created, for example, during surgery for an intestinal disorder, such as colon cancer, in which it had been necessary to remove or otherwise incapacitate the patient's rectum, leaving the patient without the natural means for controlling waste discharge. Collection bags for attachment to the human body for collecting body wastes are often referred to as ostomy bags (or as ostomy pouches). People who have had an ileostomy or colostomy find it necessary to use the bags to help manage their uncontrolled discharge of flatus gas, liquid and fecal solid material.

Several different designs of ostomy bags are commercially available. Many are pictured in miniaturized outline form and described in detail in commercial catalogs, for example, from Edgepark Surgical, of Twinsburg, Ohio, a company that sells ostomy products from several different manufacturers. Commercially available ostomy bags come in various sizes and shapes generally ranging from about 10 to 15 cm (4 and one half to 6 in.) wide, and about 10 to 25 cm (6 to 10 inches) long, or even longer if the bag has a discharge channel. Such bags usually comprise a body-side wall (i.e. intended to face, be nearer to, the user's body, sometimes referred to herein as the proximal wall or rear wall) and an opposing frontal-side wall (sometimes referred to herein as the distal wall or frontal wall). Each of these walls normally has a base that is a gas- and liquid-impermeable, heat sealable thermoplastic material. The internal surfaces of the frontal-side and body-side wall materials are sealed to each other at or near their perimeters, thus defining an interior chamber of the bag between the walls. The proximal walls of commonly used bags have near the top of each bag (as it is worn by the user) a circular stomal aperture. In a bag referred to as a two piece bag, that aperture is circumscribed by a relatively firm plastic ring, for attachment to a mating ring of an ostomy wafer that is adhesively attached to the skin surrounding the stoma. The attachment of the two rings is intended to provide a liquid and gas impermeable junction. One of the most common attachments uses a protruding, male circular ring member on the ostomy wafer and a female circular recess on the ostomy bag. As the rings are mated with pressure applied the rings snap into mating connection with the plastic protruding ring surrounding the proximal wall stomal aperture. In a corresponding "one piece bag" the means for attachment of the bag directly to the body is an integral part of the bag. But for the thickness of the ring member or other attachment means, most currently available ostomy bags as viewed from an edge are approximately the thickness of a fine line drawn by a fine line pen. Accordingly, even though such bags are described in recent art as having "chambers," until something enters the bag the chambers really are two face-to-face flat pieces of plastic sealed around their perimeter. From a word precision standpoint such bags could be said to be a "latent chamber" or have a "chamber precursor." That is, (except where and to the extent the walls are sealed together and where appropriate port closure is provided) such bags have opposing walls that are readily separated from each other, for example, when gas, liquid and/or solids enter the bag. The result of the material entering the bag is to develop the three-dimensional character of the "chamber", i.e. convert the chamber precursor into a chamber. This distinction has importance that will be discussed further below. For purposes of clarity, when the term "chamber" is used herein (unless otherwise indicated) the term is intended to include both "chamber precursor" and "chamber".

The art generally refers to ostomy bags as one piece or two piece, and drainable or closed. Drainable ostomy bags usually have a narrowed, elongated portion ending in a discharge opening at the bottom of the bag. The narrowed, elongated portion accommodates closure members such as those described in U.S. Pat. No. 6,336,918. Such bags are normally closed by folding the narrowed portion over a blade of a removable closure device and forcing the blade and folded portion into a mating crevice in the device to form a gas and liquid impermeable closure. Closed bags have no opening at the end of the bag and are normally used in situations where the bag is either discarded after use or removed temporarily for washing.

Prior art devices have attempted to make the use of ostomy bags more comfortable to users, referred to herein as ostomists. One improvement that has been made, for example, is to include a comfort layer, a thin external layer of flexible, "breathable" fabric or thermoplastic covering the external surface of the proximal wall that would routinely come into contact with the body of the ostomist. Such a comfort layer reduces the discomfort of the plastic against skin feeling.

Many ostomists try to live a normal lifestyle and can, indeed, be very active. Nonetheless, even for those who are justifiably optimistic because they have beaten a deadly disease like colon cancer, problems persist. For example, for ostomists there is a whole new definition for the term "waste management!" Some of the most significant challenges ostomists face are associated with handling their personal day-to-day waste management chores and situations. Shortly after becoming one, an ostomist is quickly slapped in the face with first hand knowledge that some "natural products" are not pleasant, and that the smog index is not their most important air quality problem. The ostomist in public life has to be aware of his or her ostomy bag and the extent to which it is leaking its vile odors to the surrounds. Odor control or avoidance is still a major air quality challenge facing the ostomist, whether the ostomist is in a car pool, an office, an all day business meeting, a dinner party, or at home with the family! Controlling the problems associated with flatus gasses can be a particularly difficult challenge for those who still have a major portion of their small intestine but have had a significant portion of their large intestine removed. Evidently, because of the increased probability of flatulence and because the smell of the gas is extraordinarily foul, a number of attempts have been made to provide the ostomist confidence and comfort in controlling emission into and out of the ostomy bags. U.S. Pat. No. 6,135,986 ('986), for example, describes a number of prior art attempts to include filters and venting systems to deal with these problems. The patent (986) also outlines shortcomings of those prior art attempts. Those prior art attempts offer some improvements for both drainable and closed ostomy bags. The proposed solutions come in a wide variety of alternatives, for example, of filtering devices. However, problems still exist. Convenience, comfort, confidence and reasonable cost are extremely important for the ostomist. Filter mechanisms get clogged, resulting in bags becoming precariously expanded or, the filters get bi-passed. Even filters placed in the upper extremity of bags tend to get clogged. When ostomists are lying down or even in a sitting position, fecal emission collects around the stoma and can plug tiny holes used in a number of prior art filter systems. Those using gas permeable membranes are particularly susceptible to this type of clogging. If the filters do not operate effectively to allow the gasses to pass through them and deodorize that gas, the filters either emit their horrible odors or inhibit gas flow causing the bag to inflate. The latter can cause leakage of gas through the otherwise reasonably secure ring "seal" connecting the bag to the wafer, or can even cause the ring seals to disconnect, and the bag to pop off the wafer. The result is the release of foul smelling flatus gas, or worse! In addition, the solutions offered in the prior art (including in the '986 patent) tend to be relatively expensive. This is a critical factor to most ostomists and their insurers.

Even though a major ongoing concern for the ostomist is associated with flatus gasses, using an ostomy bag with no filter is still the option of choice of many less than content ostomists. As indicated above, the no filter or plugged filter alternatives leave the ostomist with an uncomfortable and sometimes embarrassing need, that of manually venting (deflating) the bag. Manual venting systems described in the prior art, for example, those described in U.S. Pat. Nos. 5,693,035, and 2,054,535 tend to be somewhat cumbersome and costly, thus limiting their acceptance. Accordingly, manual venting is routinely accomplished by many ostomists through the sequential steps including: (a) seeking and finding a private location; (b) opening or raising a garment (thereby exposing the top of the wafer/bag ring connection); (c) opening the connection partially (thereby breaking the original seal between the bag ring and the wafer ring; (d) applying slight pressure on the bag to release the gas into the atmosphere; (e) snapping the connection into complete closure; and, then (f) flapping the garment to fan the odor away. However, the odor is not one to release in a friend's bathroom! Even very strong bathroom ventilators are inadequate to deal with the penetrating and lasting odor. "Experts" have suggested lighting matches or candles. They help, but not adequately, and not at all in "no smoking" public toilet areas. Then there is the problem with the odor being retained in or on an undergarment, or the flapped garment. Also, periodically breaking the seal between the wafer and bag rings can result in a weakened seal or fecal material finding its way into the seal junction thereby increasing the risk of odor leak through the seal. Odor control agents (odor counteractants) applied in the bags tend to be messy and insufficiently effective and, therefore, do not solve the problems. Thus, many ostomists choose the no filter option with no built in vent system simply because there is not an attractive cost- or functionally-effective alternative. Some ostomists even choose fasting before a social event and/or avoidance of socialization to avoid creating uncomfortable situations for others and personal embarrassment. That, too, is not practical in the real, everyday work world.

One of the more distasteful, regular routines that many ostomists are confronted with is that of emptying the ostomy bag. This procedure puts the ostomist's nose in much closer proximity to his or her waste than any would like, and closer than most any non-ostomist would tolerate. There is a need to pay close attention to what one is doing in the emptying process, or such waste can find its way to many more places than anyone would like. There have been apparatus and techniques for facilitating bag cleaning disclosed in the prior art, which would help increase the nose/waste distance. (See, for example, U.S. Pat. No. 5,470,325 and references cited therein.) However, these have tended to add significant additional cost, and prior art cleaning devices (such as are described in U.S. Pat. Nos. 6,532,971, 5,083,580 and 5,037,408) generally would be cumbersome to make available outside the ostomist's home bathroom and/or add distasteful steps to the ostomist's routine. Some of the smell is associated with the emptying of drainable bags and especially the cleaning of the drainage channel after emptying.

The ostomist in need of deflation is pushed by the above challenges in the direction of interrupting normal activities and finding seclusion to go through the steps indicated above to minimize, and hopefully avoid, discomfort and embarrassment from escaping odors, fluids, and/or solids. Ostomists are left wanting for an ideal system for handling their ostomic environment (that is, the odors, the discharges, the discomfort, the appearance, the inconvenience, and the health issues) to minimize the negatives for their friends, family and associates, while being thankful that the surgery that created their ostomy likely saved their life.

BRIEF SUMMARY OF THE INVENTION

In accordance with the present invention the ostomist is offered processes and systems, including tools, for managing ostomic waste which accommodate a wide range of physical dexterity limits and social situations, while helping to minimize the personal risks to the comfort of others as well as themselves (e.g. to the ostomist's employment security and to social acceptability). The present invention offers significant, added flexibility to ostomists as to how to deal with their very personal, often troubling issues. The ostomy waste management tools processes and systems, including ostomy bags and versatile latent tubes, of this invention provide this flexibility cost effectively and conveniently with little adjustment to the ostomist's routine. In addition, this invention could simplify the manufacturing process for manufacturing ostomy bags that suit a number of differing purposes, while offering the ostomist unprecedented choices. Making flushing cleaner and easier to accomplish accordance with the present invention can result in less high smell time adding further comfort to the ostomist. Bags or pouches in accordance with this invention having latent multiple use tubes (versatile tubes) having ports that accommodate those multiple uses also allow the ostomist to benefit more efficiently and reliably from existing products and previously suggested concepts from others, for example, for de-odorizing flatus gasses.

A BRIEF DESCRIPTION OF THE DRAWINGS

The figures described below depict various preferred aspects in accordance with the subject invention. The figures are for illustration and are not drawn to scale. For example, where walls are sealed together, wide or hatched lines represent the seals. The width of those seals is exaggerated to assist in displaying certain characteristics. Similarly, proportions do not necessarily conform to any commercial ostomy bags. Dimensions have been selected to represent specific features for illustration, while sized and proportioned to fit drawings that will illustrate the inventions discussed. The many different sizes and shapes of commercially available ostomy bags testify to the differences of opinions of skilled artisans in this area. FIGS. 1, 2, 3, 4, 6 and 7 are depicted in the orientation in which they would appear if they were viewed from the front of an ostomy bag wearer (ostomist). Accordingly, even when in partial or cutaway, unless otherwise indicated, their orientation would appear the same way. Viewed in that way, some commercially available bags have arched tops and arched bottoms, while others have arched tops and relatively straight, horizontal bottoms. Still others have narrowed bottoms with discharge openings. Some ostomy bags have relatively straight-line, horizontal tops and arched bottoms. Some appear as ovals, others as rounded corner rectangles or trapezoids. The list goes on. The drawings and descriptions below are intended to illustrate that these same types of bag configuration alternatives are accommodated and benefited by the present invention. Thus, for example, where an upper extremity of a bag is depicted and described below in accordance with the present invention, unless otherwise specifically stated, the upper extremity would provide benefit when used with bottoms of any practical shape. Also, the term "multiple use tube" as used herein includes versatile tubes, that is, tubes have the potential for being used for a number of separate purposes, but not necessarily actually used for multiple purposes. Accordingly, a specific user may use a particular multiple use tube as described hereinbelow for the same purpose continually, while another user may use an identical tube for a different purpose. Yet another user may choose to use an identical tube for two or more purposes. Such tubes all fall within the definition of "multiple use tube" or "versatile tube" as used herein.

FIGS. 8 (A, B, C, D, E and F) depict some tools for use by the ostomist consistent with the depiction in FIG. 7.

DETAILED DESCRIPTION OF THE EXEMPLARY EMBODIMENTS

Figure 1:
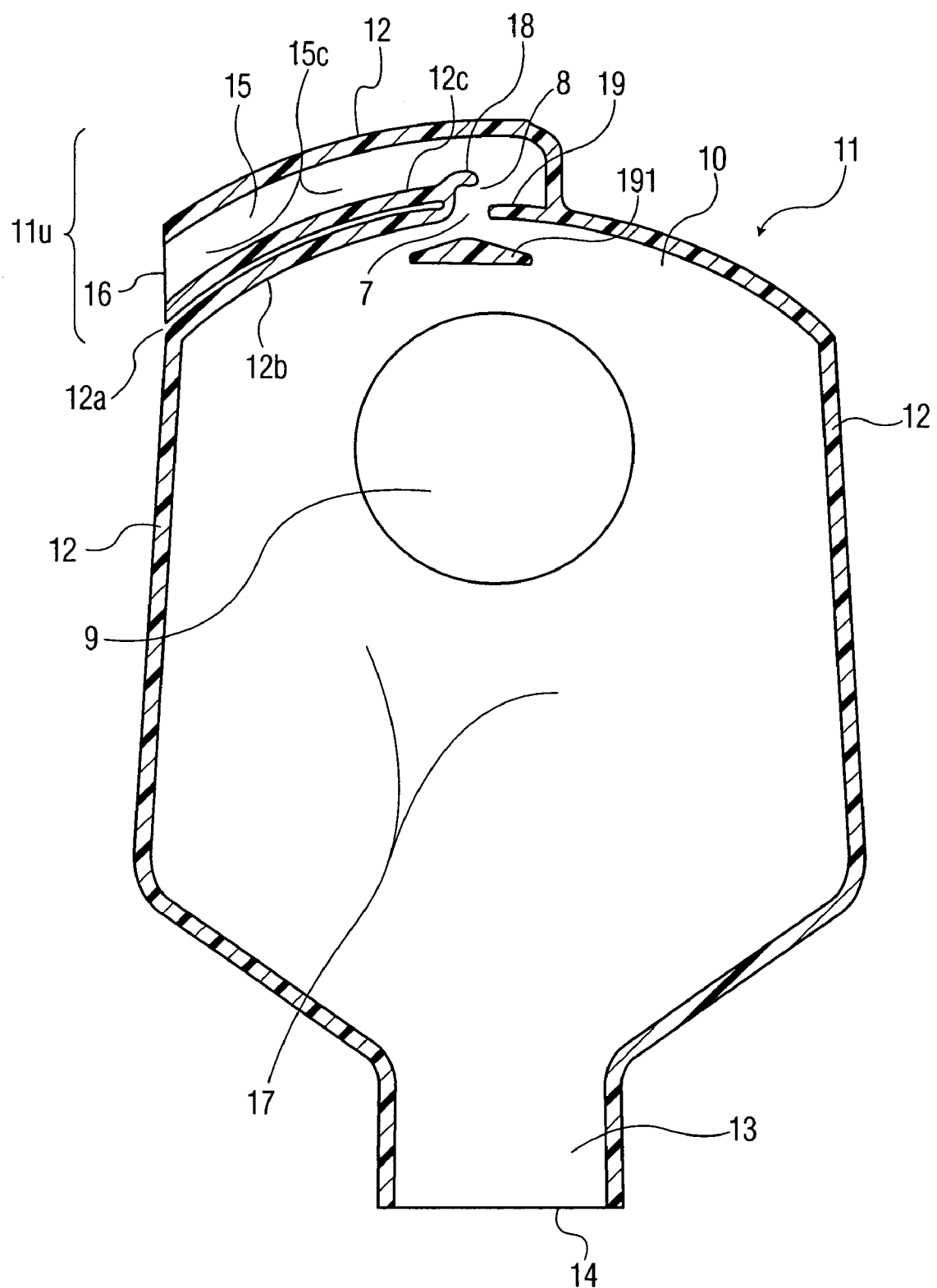
FIG. 1 depicts in cutaway outline the internal surface, with sealed perimeter and internal surfaces and unsealed perimeter edges, of the body side-wall of a drainable ostomy bag. The full perimeter of FIG. 1 depicts the frontal outline view of the bag.

FIG. 1 depicts, in cutaway drainable ostomy bag 11 revealing interior surface of the body-side wall 10 of ostomy bag 11 having an arched top. As indicated above, the body-side (or "rear") wall is the wall of the bag that is normally closest to the skin of the ostomist wearing the bag. The exterior of rear wall 10, therefore, is desirably (and typically) covered with a soft textured more skin friendly plastic. Ostomy bag 11 rear wall 10 has a perimeter that is sealed to a mating frontal-side wall and to a partially mating comfort layer on its exterior. The seal is indicated by hatched lines: seal 12, seal 12b, and seal 12c. The entire perimeter of ostomy bag 11 is sealed except for two ports: (1) waste discharge port 14 and (2) versatile tube multipurpose port 16. Port 14 is the opening at the end of waste discharge channel 13. During waste collection in main chamber 17 of ostomy bag 11, (the chamber receiving gaseous, solid and liquid waste from the stoma) channel 13 is closed, for example, using clamps readily available in the market. (See, for example, U.S. Pat. No. 5,125,133.) Channel 13 is opened at times of discharge of waste through port 14 and during cycles of cleaning bag 11 when the bag is drained through channel 13, the fluid exiting out port 14. Port 16 is a transverse or crosscut opening at the end of versatile tube 15. The terms "transverse" and "crosscut" as used herein with respect to tube openings mean openings completely across the tube (or that would result in open end shape profiles, rather than longitudinal openings in the tube walls), but not limited to openings across at right angles to the tube walls. The fact that versatile tube ports which open to the outside of ostomy bag 11 are transverse (or crosscut) openings is important to the tubes' capability to accommodate the insertion of connectors, filters or other ostomy tools described herein. The principle is that the versatile tube can accommodate insertion and support secure connection of tools and thus it can be said that the distal opening of the versatile tube "will support axial flow," more than radial flow, of gas out of the opening, (that is, flow more in the direction of the longitudinal axis of the versatile tube than in the direction of the radius of the tube). Without versatile tube 15 and its chamber 15c, and the baffles associated with it, ostomy bag 11 looks very much like bags that are commercially available. The inclusion of a versatile tube like tube 15 in a new bag designed to include it would, except for initial retooling costs, involve minimal additional manufacturing cost. Yet, that small addition to the structure of the bag, adding a versatile tube, provides substantial benefits to ostomists. This will be discussed more fully below. Stomal aperture 9 represents a commonly used opening in an ostomy bag rear wall through which a normal stoma can protrude, and through which stomal waste is deposited in main chamber 17 of bag 11. Upper extremity 11u of ostomy bag 11 for purposes herein is defined in the context of the bag as worn. Thus, the area above the actual stoma (the "upper extremity of the bag") would usually begin at a level at least about 1 cm (⅜ inch) above the level of the midpoint of an actual rear wall aperture. Similarly, "upper extremity of main chamber 17" would be that portion of the main chamber above a level at least about 1 cm above the level of the midpoint of the rear wall aperture.

Fluid communication between the upper extremity of main chamber 17 and latent chamber 15c of versatile tube 15 is supported through port 7. Versatile tube 15 is sealed on its upper perimeter by a portion of seal 12 and on its lower perimeter by seal 12c. That upper portion of seal 12, together with baffle 19, port 7, seal 12c and distal port 16 define the boundaries of versatile tube 15 chamber 15c. Arched space 12a is an exaggerated depiction to show that seal 12c is not connected to seal 12b except at the ends of seals 12b and 12c proximal port 7. There the two ends meet and form one sidewall of port 7. The port end of baffle 19 forms the other sidewall of port 7. Optional, but desirable, baffles 18, 19 and 191 (sealed to both rear wall 10 and the frontal wall of ostomy bag 11) guide gas through channels leading to and through port 7 and channel 8 to versatile tube 15, while assisting in the prevention of fecal material getting into chamber 15c. Chamber 15c can be closed temporarily anywhere along its length with a simple clip, for example, a small bag clip, a toy hair clip, or even a paper clip (such as a small vinyl coated paper clip or a round plastic paper clip). Closing port 7 (and/or channel 8) temporarily would keep fecal matter from finding its way into chamber 15c of tube 15. Prior to using tube 15, for example, as a vent tube, space in the upper extremity of chamber 17 near port 7 would be cleared of any fecal matter. In the unlikely event solid or liquid fecal material does get into chamber 15c, the ostomist can readily remove it. After first assuring the closure of port 16 and fixing the distal end of tube 15, the ostomist uses his or her left thumb and forefinger to squeeze tube 15 while moving the thumb and finger in the direction away from port 16 and toward port 7. When the material gets to the channel 8 side of baffle 18 the squeezing moves in a downward direction and then toward, and past port 7 so the material passes into the upper extremity of chamber 17, down and away from port 7. Baffles 18 and 19 are shaped to provide both resistance to fecal solids getting into chamber 15c and to facilitate the squeezing out of any fecal matter that does get past port 7 and toward or into chamber 15c.

In a preferred embodiment versatile tube 15 is included in the manufacture of bag 11 (substantially simultaneous) in much the same way as conventional manufacturing handles the manufacture of the narrowed area waste discharge channels analogous to channel 13. That is, tube fifteen is manufactured from the same set of blank plastic sheets (or rolls) as is used for forming main chamber 17 and discharge channel 13. Thus, the front and rear walls of main chamber 17, discharge channel 13, and versatile tube 15 are of the same thickness, texture and flexibility. However, as is the case with some well known commercially available bags the comfort layer that covers the exterior of the rear wall of their main chamber, covers only a small portion of the rear wall of the narrowed discharge channel. In one commercially available bag, for example, the narrowed waste discharge channel area has parallel sealed edges extending in length about 5.5 cm (about 2.2 in.) with about 4.5 cm (about 1.8 in) of that length nearest the exit port having no comfort backing. For reasons discussed below it is helpful to have no comfort covering on at least about 1.2 cm (about 0.5 in.) of the end length of versatile tube 15 nearest exit port 16. Versatile tube 15 can be used for such purposes as: (a) connecting to firm tubing used as connectors or filters; (b) connecting directly to filters; (c) venting of flatus gasses; (d) partly or wholly housing a filter; (e) providing expansion potential to capture gas once the ostomy bag is otherwise at capacity; (f) serving as a conduit to conduct fluid from one location to another; (g) connecting to water sources for flushing waste from an ostomy bag; and (h) inserting odor counteractants or modifiers into the bag. These subjects will be discussed in greater detail in the context of subsequent drawings.

Figure 2:
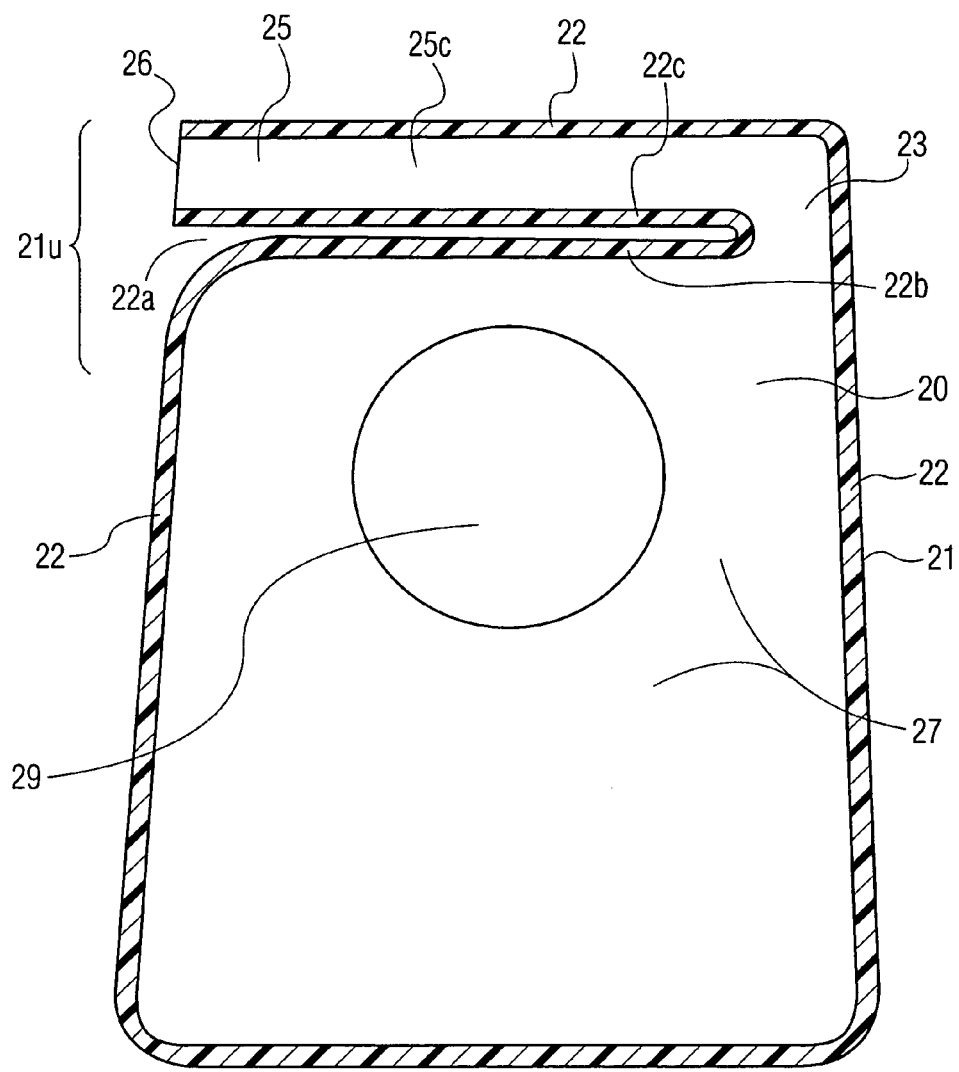
FIG. 2 depicts in cutaway outline the internal surface, with sealed perimeter surfaces and unsealed perimeter edge of the body-side wall, of a closed ostomy bag. The full perimeter of FIG. 2 depicts the frontal outline view of the bag.

FIG. 2 depicts in cutaway outline the internal surface of body-side wall 20 of ostomy bag 21 which has a rounded-corner rectangular-like perimeter and upper extremity 21u, with sealed perimeter edges (seals 22, 22b and versatile tube 25 lower perimeter seal 22c all represented by hatched lines) and unsealed perimeter edge (port 26). The full perimeter of FIG. 2 depicts the frontal outline view of ostomy bag 21. Ostomy bag 21 depicts a closed ostomy bag, thus having stomal aperture 29 but having neither a waste discharge outlet (corresponding to port 14 of FIG. 1 nor a narrow channel (corresponding to waste discharge channel 13 of FIG. 1). As previously indicated both closed and drainable ostomy bags have been made available in a number of different shapes. For example, both drainable and closed types of bags can be made available with arched profile upper extremities (similar to the upper extremity of main chamber 17 of ostomy bag 11 of FIG. 1) or generally straight profile upper extremities as depicted in the upper extremity of main chamber 27 of FIG. 2 (both as viewed from the front). Versatile tube 25 of ostomy bag 21 comprises latent chamber 25c, which is formed by a portion of seal 22 (on its upper edge and its end proximal channel 23), seal 22c and multipurpose port 26. Space 22a is an exaggerated depiction to show that seal 22c is not connected to seat 22b except at the ends of seals 22b and 22c proximate channel 23. Channel 23 is formed between a portion of seal 22 and the joined ends of seals 22b and 22c distal from port 26. Channel 23 serves as a fluid communication connection of chamber 25c of tube 25 with the upper extremity of chamber 27. The length of versatile tube 25 as compared, for example, to versatile tube 15 of FIG. 1 provides advantages for the ostomist who for example wants to use the tube for housing elongated filter material. Further consideration of such alternatives is discussed below. Ostomy bag 21 could be used for example, in many of the ways indicated: (a) for versatile tube 15 of bag 11 of FIG. 1; and (b) in the discussion of the combinations depicted in FIG. 6B below. The flat top profile upper extremity could be used to advantage with a format that would use other lower bag designs, e.g., drainable bags. The inclusion of the versatile tube in a flat top bag offers significant added options for the ostomist.

Figure 3:
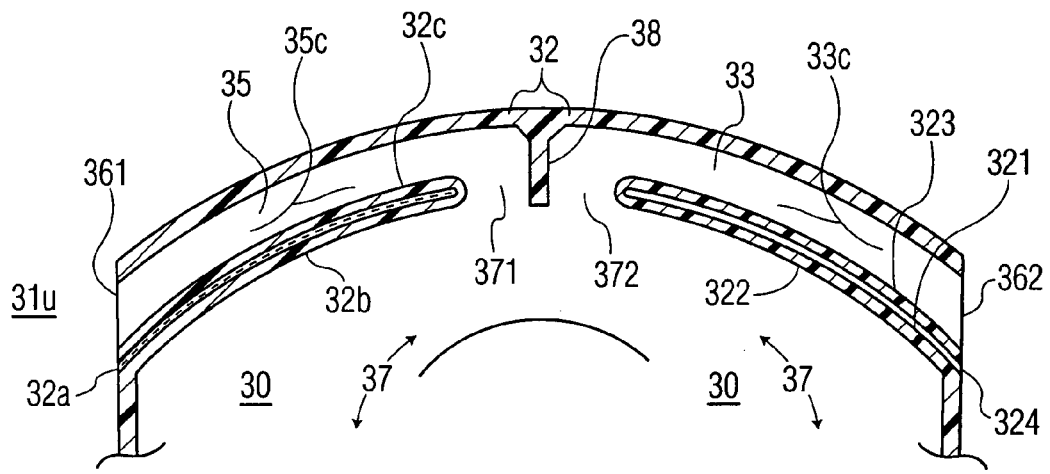
FIG. 3 depicts in cutaway the internal surface, with sealed surfaces and unsealed edges, of the body-side wall of an upper extremity of an ostomy bag having two latent, multiple use tubes.

FIG. 3 depicts in cutaway the internal surface of rear wall 30 (the body-side wall) of upper extremity 31u of an ostomy bag having main chamber 37 (partially depicted) and two latent multipurpose tubes, tube 33 on the right side (as depicted) and tube 35 on the left side (as depicted). Multipurpose tube 35 is formed by: the bag's frontal (not depicted) and rear walls, seal 38 which separates tube 33 from tube 35; a part of the upper portion of seal 32 at its top edge; multipurpose port 361; and seal 32c (which extends from its distal end at multipurpose port 361 to its proximal end at port 371). Port 371 provides fluid communication between tube chamber 35c and the ostomy bag main chamber 37 (partially depicted). The perimeter of multipurpose tube 33 is formed by: seal 38 which separates tube 33 from tube 35; a part of the upper portion of seal 32 at its top edge; distal port 362; and seal 323 which extends from its distal end at multipurpose port 362 to its proximal end at port 372 which provides fluid communication between tube chamber 33c and the ostomy bag main chamber 37. The proximal end of seal 323 connects at port 372 with the proximal end of seal 322. Along their lengths seal 322 and 323 are separated by space 321 (exaggerated to illustrate the separation). For the ostomist a bag having an upper extremity with two such multipurpose tubes provides benefit when used as a part of an ostomy bag having for the remainder of its perimeter any practical shape, for example, like those currently available commercially. For example, if tube 35 is in use, e.g., housing or connecting to a filter, or connected to another tube (e.g. for venting), tube 35 could be closed near port 371 by attaching a clip across the gap between perimeter seal 32 and perimeter seal 32c while the tube 33 is used as an entry point for a water source to flush the bag. A flushing tool is shown engaged with a similar tube in FIG. 16 and is discussed further below. Another alternative use for a second tube is for the insertion of an odor counteractant. One or more baffles, for example, similar in shape and placement (relative to fluid flow channels) to baffle 191 of ostomy bag 11 of FIG. 1, could be added to the configuration to help minimize solid fecal matter entry into chambers 35c and 33c.

Some ostomists would benefit significantly from the stability advantage provided by separable linkage 32a between seal 32c and seal 32b. The separable linkage allows the ostomist (for example who is using the versatile tube in an application that benefits from stability) to benefit from the linkage, but also allows separation by the ostomist who benefits more from a tube separated for some length back toward channel 371. This provides ostomists additional non-confusing flexibility with how they meet their needs.

With the separable seal the ostomist could leave it in place, release it part way, or separate it all the way to the junction of 32b and 32c. Among other justifications for the differing choices as to the length of the separation of the versatile tube from the main chamber perimeter would be: the use the tube is to serve (e.g. venting, filtering etc.); the specific tools intended for use (e.g. filter, conveyance tube, etc.); and the direction the outlet needs to face. For example, if an ostomy belt is worn, the ostomist might like to use a series of filters connected to the ostomy belt (see FIG. 7 and discussion thereof). In that case distal end 361 of tube 35 should point toward the belt. Belts may be positioned differently, relative to the bag upper extremity, for various bags of different manufacture. If relatively short multipurpose tube 35, for example, were to be used in connecting to a tool attached to an ostomy belt that connected high on a wafer, a full release might be required. A release of 20 percent might be appropriate for a connection to a separate filter. That 20 percent is considered to be at least a substantial part of the tube length, especially if the release provided significant benefit to the user. Accordingly, tube 35 may point straight at the belt (in which case the tube end would remain at least partially attached); or tube 35 may need to be angled either up or down (in which case the tube 35 could be separated all the way to the junction of 32b and 32c). So separated tube 35 would have capability substantially identical to tube 33 which, along its perimeter edge 323, is already separated from seal 322 by arched separation 321 except (a) at the juncture of seal 323 with seal 322 proximal port 372, and (b) at the distal end of seal 323 where extremely small line seal 324 helps hold tube 33 in place, e.g. during shipping. The ostomy bag thus depicted (partially) in FIG. 3 includes main bag chamber 37 with upper extremity 31u with two main bag chamber upper perimeter segments 32b and 322 of defined length with an upper perimeter seal along each. This upper extremity also has two multiple use tubes of defined length (35 and 33) and having proximal end openings (371 and 372 respectively) into main bag chamber 37. Openings 371 and 372 provide capability for fluid communication between the tubes and the main bag chamber. Each of the multiple use tubes (versatile tubes) also has a distal end (361 and 362 respectively) and a lower perimeter seal (32c and 323 respectively) proximate an upper perimeter seal (32b and 322 respectively) of main bag chamber 37. The respective upper and lower perimeter seals are proximate reaching from their distal ends to respective openings 371 and 372. The bag upper perimeter seal 32b is firmly connected to tube lower perimeter seal 32c only at their ends proximate port 371 where they form the border of port (opening 371). Similarly, bag upper perimeter seal 322 is firmly connected to tube lower perimeter seal 323 only at their ends proximate port 372, thus forming the border of port (opening) 372. Other than at their juncture at the port borders each of the upper and lower border pairs are less than firmly connected along a significant length (in fact along their entire length) of the upper and lower seals' proximity in the direction of the respective tube's tube distal end. That is, along its entire length (except for the juncture at their ends proximal port 371) perimeter seal 32b is releasably (or separably) attached to seal 32c, whereas seal 322 is unconnected to seal 323 along its length except (a) at their joined ends which form one border of port 372, and (b) at the weak, line seal. For purposes herein releasably or separably connected seals and seals less than firmly connected shall mean a connection that has a clearly defined path of separating as would be necessary to avoid accidental rupture or weakening of vapor tight seals. For example, a clearly defined thinning in a wider than normal seal, a clearly indicated perforating of a sealed area (or between sealed areas), or even a widened seal area (or two closely adjacent seals) with a clearly defined path for separation would fit the definition of "less than firm connection", of "separably connected", and of "releaseably connected". For many applications, arched tubes (e.g. tube 15 of FIG. 1, and tubes 35 and 33 of FIG. 3) can be used in place of straight line tubes (such as tube 25 of FIG. 2) and vice versa. Manufacturing efficiencies can drive choices to one shape or another. Thus, a two tube ostomy bag can have straight-line tubes, for example, as illustrated if FIG. 7 below. It is also important, however, in accordance with one aspect of the present invention that at least one distal port (that is, the distal tube end) be transverse to the tube axial flow (capable of axial gas flow out of the tube opening) to accommodate secure tool insertion.

Figure 4:
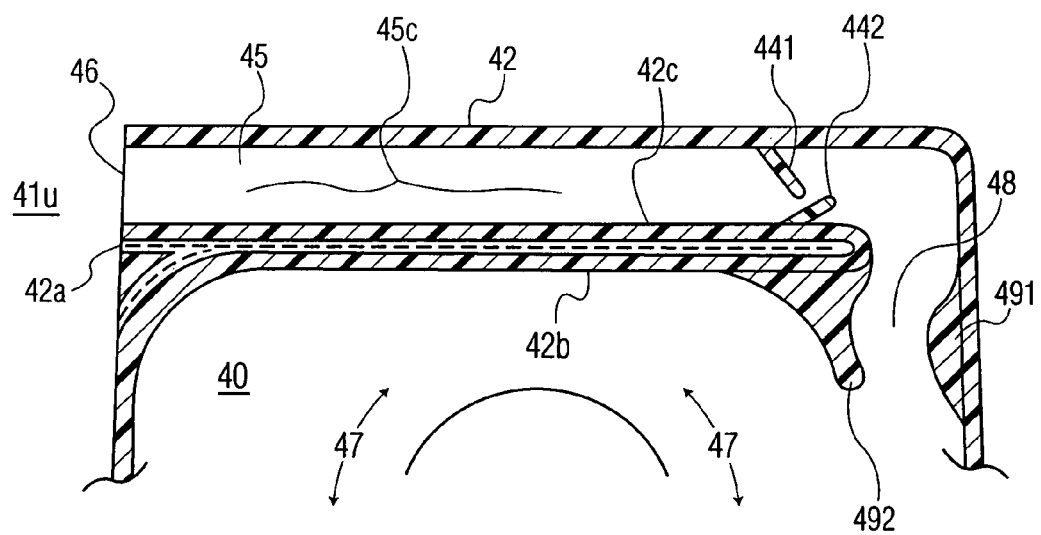
FIG. 4 depicts, in cutaway outline the internal surface, with sealed surfaces and unsealed edge of the body-side wall, of the upper extremity of an ostomy bag having a generally straight line top.
Figure 8A:
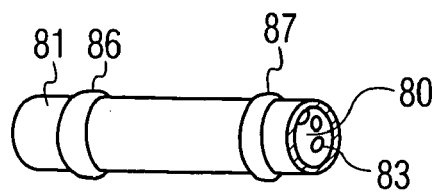
FIG. 8A depicts a cylindrical filter.
Figure 8B:
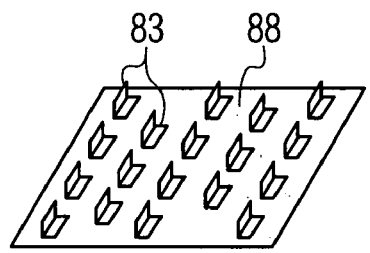
FIG. 8B depicts in fragmentary perspective filter material before it is rolled as an interior component of a filter.
Figure 8C:
FIG. 8C depicts an enlarged view of a latent tube connector.
Figure 8D:
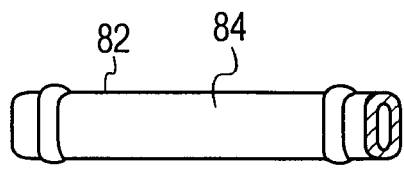
FIG. 8D depicts a connector having a relatively flat, slender, elliptical-profile.

FIG. 4 depicts in cutaway the internal surface of the rear wall 40 (the body-side wall) of upper extremity 41$u$ of an ostomy bag having a long, substantially horizontal straight-line (as depicted) multipurpose tube 45, which is formed by: frontal wall (not depicted) and body side wall 40; the upper portion of seal 42; distal port 46; and seal 42$c$ which ends at channel 48. Channel 48 provides fluid communication between tube chamber 45$c$ and the ostomy bag main chamber 47 (partially depicted). A bag having a long multipurpose tube would provide benefit to an ostomist, for example, when the tube is used to house a series of removable cylindrical filters, for example as illustrated in FIG. 8A below. Advantageously, baffles 491 and 492 would deflect most fecal solid or liquid that otherwise could enter channel 48. The long versatile tube would also permit facile removal (See discussion on FIG. 3.) should any such matter get into chamber 45$c$. The length of versatile tube also permits the inclusion of baffles 441 and 442 upstream of normal gaseous flow to further impede the flow of fecal solids that otherwise could touch or even clog the filters. These optional, but advantageous baffles 441 and 442 are ideally anchored at opposing perimeter seals 42 and 42$c$ and leaning somewhat in the upstream direction (back toward channel 48). The separable linkage 42$a$ linking seal 42$c$ with seal 42$b$ provides the flexibility referred to above with respect to separable linkage 32$a$ of FIG. 3. Separable linkage 42$a$ is depicted as extending to the end of seals 42$c$ and 42$b$. However, in some circumstances it may be appropriate to have the separablilty extend only a substantial distance (e.g. 30 percent of the distance) from the distal end of tube 45. That option exists for other separable linkages in accordance with the present invention. The distance of separation desired would depend, for example, on the total length of the versatile tube and the particular use chosen for the versatile tube. Again, an ostomy bag having for the remainder of its perimeter any practical shape, for example, like those currently commercially available, could benefit from having the upper extremity depicted in FIG. 4.

Figure 5A:
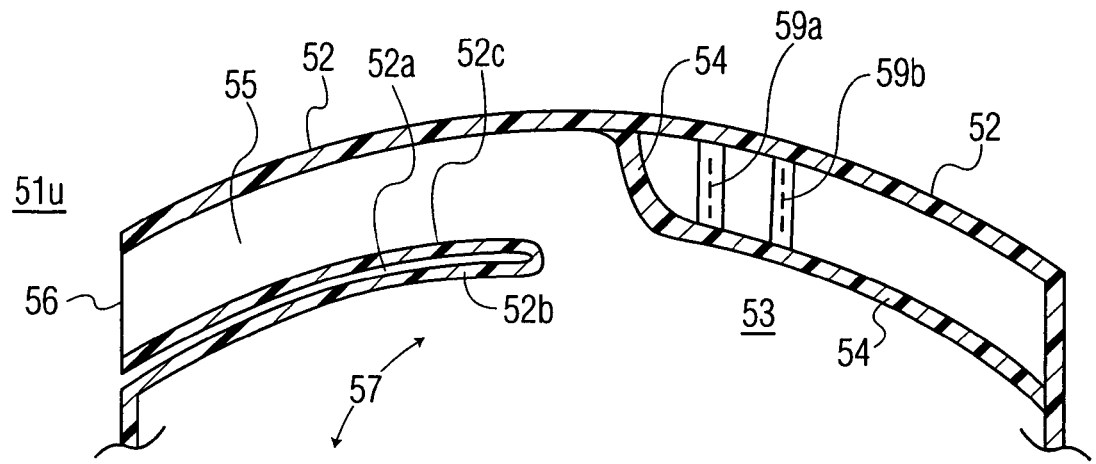
FIG. 5A depicts, with sealed perimeter surfaces and unsealed perimeter edges, the upper extremity of the external side of the frontal wall of an arched top ostomy bag having a versatile latent tube and an internal closure mechanism for closing the tube.
Figure 5B:
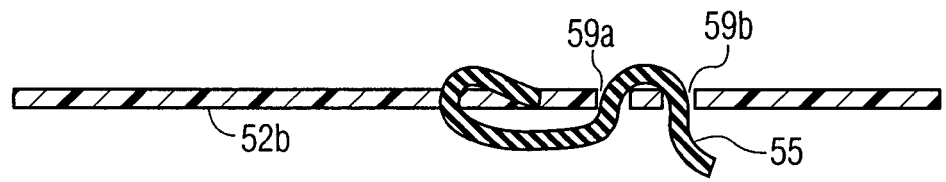
FIG. 5B and FIG. 5C depict in top view cutaway the ostomy bag of FIG. 5A illustrating the formed closure mechanism, each with the versatile latent tube in different closed positions.
Figure 5C:
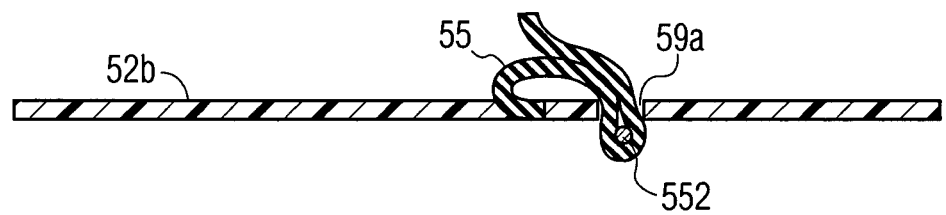

FIG. 5A depicts upper extremity 51$u$ of the external side of the frontal wall 53 of ostomy bag upper extremity 51$u$, with sealed perimeter surfaces 52, 52$b$, 52$c$ and a portion of internal boundary seal 54, together with unsealed perimeter edge, multipurpose port 56 forming the perimeter boundaries of versatile tube 55 which fluidly communicates with main bag chamber 57. A portion of perimeter seal 52 together with internal boundary seal 54 provide boundary of the internal closure mechanism, which further includes slits 59$a$ and 59$b$. Boundary seals along slits 59$a$ and 59$b$ provide strength for the closure mechanism. Depending on the application (for example, frequency of opening and closing) it could be advantageous to include internal seals on both sides of each slit, extending the full length of the distance between perimeter seal 52 and internal boundary seal 54 to provide additional strength for slit integrity. FIG. 5B depicts the integrally formed closure mechanism of ostomy bag 11 in exaggerated/magnified cutaway showing the path of tube 55, first through slit 59$a$ and then through slit 59$b$ as one way to close tube 55 using the internal closure mechanism. FIG. 5C depicts in exaggerated/magnified cutaway the path of tube 55, first folded (doubled) over and then (the fold is) advanced through slit 59$a$ as another way to close tube 55 using the internal closure mechanism. If desired, the FIG. 5 C alternative is made more secure by inserting; for example, one leg of a soft-ended paper clip 552 (e.g. a vinyl coated paper clip) in the fold after the fold is advanced through slit 59$a$.

Figure 6A:
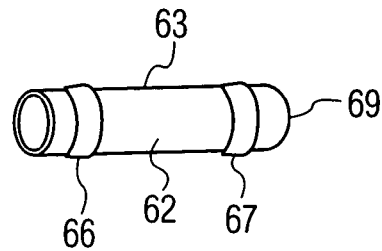
FIG. 6A depicts in perspective a connecting tube for connecting selected apparatus to an ostomy bag.
Figure 6B:
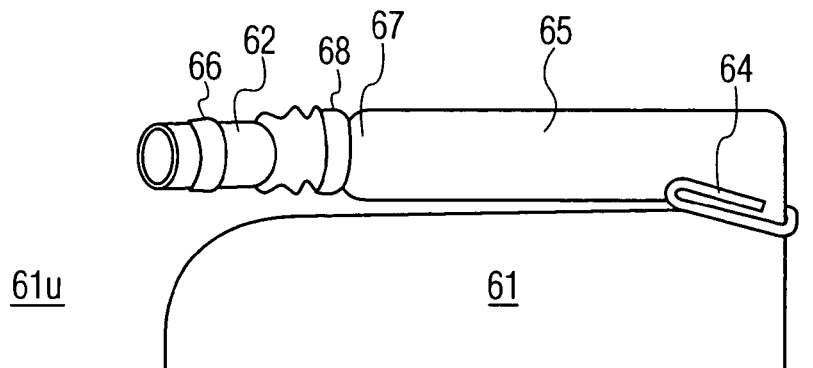
FIG. 6B depicts in perspective a partial view the upper extremity of an ostomy bag with a straight-line, horizontal top, which has a connecting tube, inserted into its multiple use tube.

FIG. 6A depicts in perspective generally cylindrical firm connecting tube 62 for connecting selected apparatus to an ostomy bag in accordance with the present invention. Attached to main cylinder 63 of connecting tube 62 near each of its ends (e.g. see proximity of hump 67 to end 69) are circumscribing rounded humps 66 and 67 having a maximum diameter (at the largest diameter of the hump at least about 2.5 mm, about 0.1 inch) greater than the exterior diameter of main cylinder 63 adjacent each hump in the direction of the cylinder toward the other hump. As depicted in perspective in FIG. 6B, connector 62 of FIG. 6A has been inserted in an axial direction (i.e. axially inserted) in versatile tube 65 of ostomy bag 61 of which only upper extremity 61$u$ is depicted (similar to upper extremity 41$u$ of FIG. 4B, except that versatile tube 65 is separated from the main chamber of bag 61 along a major portion of its edge proximal said main bag chamber). End 69 of connecting tube 62 is secured inside versatile tube 65 by elastic band 68 which is placed on the exterior of versatile tube 65, said band 68 circumscribing tube 65 and securing connector 62 end 69 within versatile tube 65. Desirably, the placement of elastic band 68 (around cylinder 63) would be proximal to, but to toward the end-to-end center point of connecting tube 62 from, hump 67. Versatile tube 65 as depicted is closed at its proximal end by placement of clip 64. Closure of versatile tube 65 would be standard procedure when connections are being made (or changed) while an ostomist is wearing the bag. It should be recognized that either or both versatile tube 65 and connecting tube 62 could house filters. This is discussed more fully in the context of FIG. 7 and FIG. 8 below.

Figure 7:
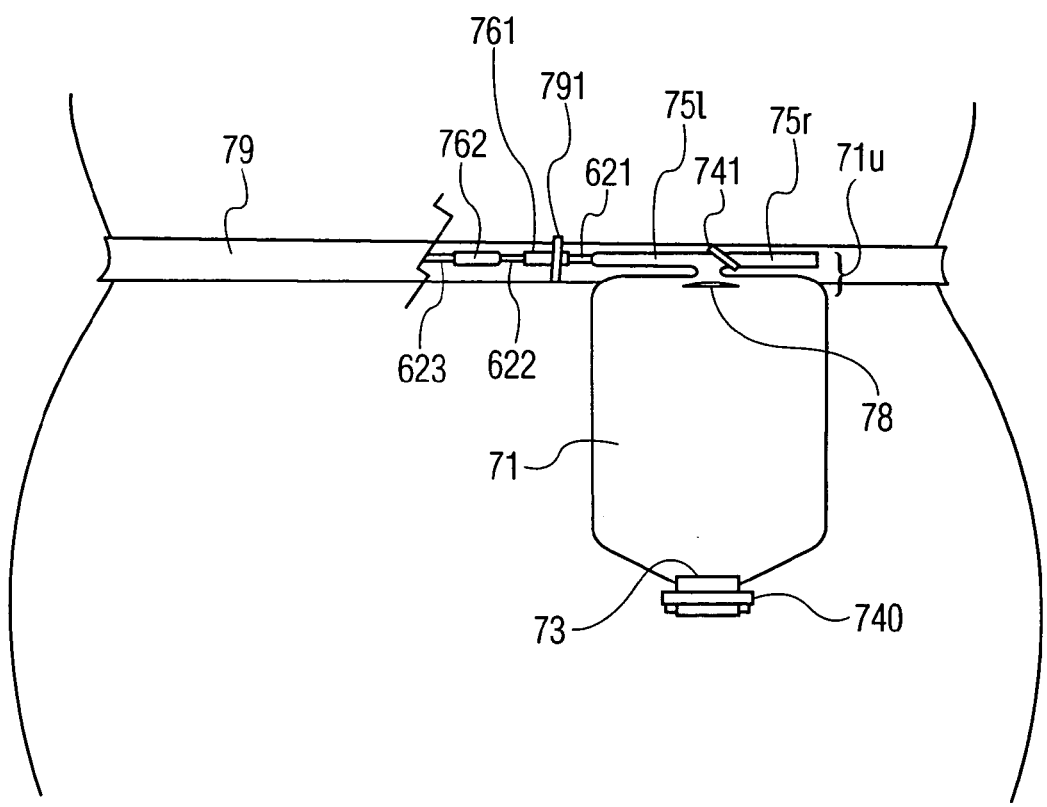
FIG. 7 depicts an ostomist's midsection with the ostomist wearing an ostomy bag (the upper extremity of which has a straight line horizontal top) having two versatile tubes, one of which is connected to some tools used by the ostomist to manage waste.

FIG. 7 depicts the midsection of an ostomist wearing ostomy belt 79 (available commercially for many ostomy bags for connection to the bag proximate the bag ring mating the connection wafer). Belt 79 gives added confidence to the ostomist, and some support to ostomy bag 71, a drainable bag which is closed at its narrowed area, waste discharge channel 73, by closure clip 740. Straight-line, horizontal topped, upper extremity 71$u$ has baffle 78, which helps to minimize the probability for fecal matter to enter its two versatile tubes, 75$l$ and 75$r$. Right side (as depicted) tube 75$r$ is closed with clip 741, as would be the case if tube 75$r$ were to be used, for example, only occasionally for such maintenance procedures as: addition of odor control material; flushing the bag; or unfiltered venting. Left side versatile tube 75$l$ is connected to tools for managing gaseous waste, e.g. by connector 621 to filter 761, both of which are supported directly or indirectly by ostomy belt 79 through the use, for example: of elastic bands, such as band 791, connected to both ostomy belt 79 and at least one of the tools (in this case filter 761); or supportive belt loops sown on ostomy belt 79 through which the tools are inserted; or hook and loop connecting pads (e.g. a hook pad sown to the belt and the loop pad adhesively attached to the tool). Filter 761 is further connected by another connector 622 to second filter 762 which is connected to another connector 623 which can be connected to another tool of the ostomist's choice (See, for example, discussion related to FIG. 13 below.) Although not illustrated in FIG. 7, first filter 761 alternatively could be connected to a different kind of filter by a latent tube connector 85 of FIG. 8C (a short version of latent tube 1301 of FIG. 13, below). The type of filter, and the numbers of filters used by each ostomist would be a matter of choice, depending upon such matters as: the effectiveness of a specific filter or combination of filters for the ostomist; the length of time the filter usually remains effective for the ostimate; or the length of time the ostomist will expect to be (e.g. in a social or business situation) without an appropriate change opportunity. If, for example, the ostomist expects to be in a serious business negotiation for several hours, or is going into an employment interview that could last for a full day, the ostomist might wish to use a series of a combination of filters that have been most effective in the past. Each filter has its limitations. Such a series of filters could best inconspicuously eliminate the chance for embarrassing and financially serious, negative consequences.

A cylindrical filter such as filter 81, depicted in FIG. 8A, can be particularly advantageous in the system and processes of the present invention. Cylindrical filter 81, desirably with circumscribing rounded humps 86 and 87 similar to those of humps 66 and 67 of connecting tube 62 of FIG. 6A, has an exterior size about the same as connecting tube 62. Accordingly, filter 81 can be used both as a connector and filter, for example, as a filter substituting for connector 62 in FIG. 6B, or as the first connector, connected to left side versatile tube 75l of ostomy bag 71 in FIG. 7, thus constituting the first in a series of filters. A glimpse of the material comprising interior 80 of filter 81 according to one preferred embodiment of the present invention is depicted through the end of filter 81 illustrating filter fingers 83 which help form and define the flow channels for gas to pass through interior 80 of filter 81. That inner material is depicted in more detail in FIG. 8B in exaggerated fragmentary perspective as irregular surfaced paper 88 having fingers 83. Cylindrical filters having interior textured surfaces for pipe smokers are well known. The cylindrical filters in accordance with one aspect of the present invention are made in the same general manner as some well known cylindrical pipe filters. However, cylindrical filters in accordance with this aspect of the instant invention have deposited within their interstices, especially in the fingers 83, an odor capturing agent such as activated charcoal for removing foul odors of flatus gasses. Latent tube 85 of FIG. 8C having the general circumferential configuration as a segment of a versatile tube, for example, versatile tube 75l of FIG. 7 is used, e.g. to connect a series of filters (e.g. cylindrical filters like filter 81 of FIG. 8A). Accordingly, the sequence of filters and connectors, at the choice of the ostomist, can be easily modified by, or example, substituting filter 81 for connector 62. Such a substitution could add hours of confidence about odor free life for the ostomist. The tube system of the present invention also allows the filters to be relatively remote from fecal matter in the bag. Even if the filter were placed in the distal end of versatile tube 75l of FIG. 7, it would be unlikely that sufficient fecal solids or liquids would bypass baffle 78 and move far enough through versatile tube 75 to damage the filter before the ostomist could squeeze the fecal matter back into main chamber 71. Moving any aggressive fecal matter back to main chamber 71 is accomplished simply and cleanly by the ostomist in private by: (a) using his or her right hand thumb and forefinger holding tube 75l close to the filter thereby closing tube 75l upstream of the filter; then (b) using his or her left hand thumb and forefinger to squeeze the tube immediately adjacent the right hand thumb and forefinger; and then (c) moving the left hand thumb and forefinger toward and past the baffles and then downward toward the main chamber of the bag. In accordance with the present invention, the distance of the filter from the collection area combined with the relatively large area for gas/filter contact also provides the opportunity for enormous increases in filter effectiveness with little bulk or inconvenience to the ostomist.

Figure 8E:
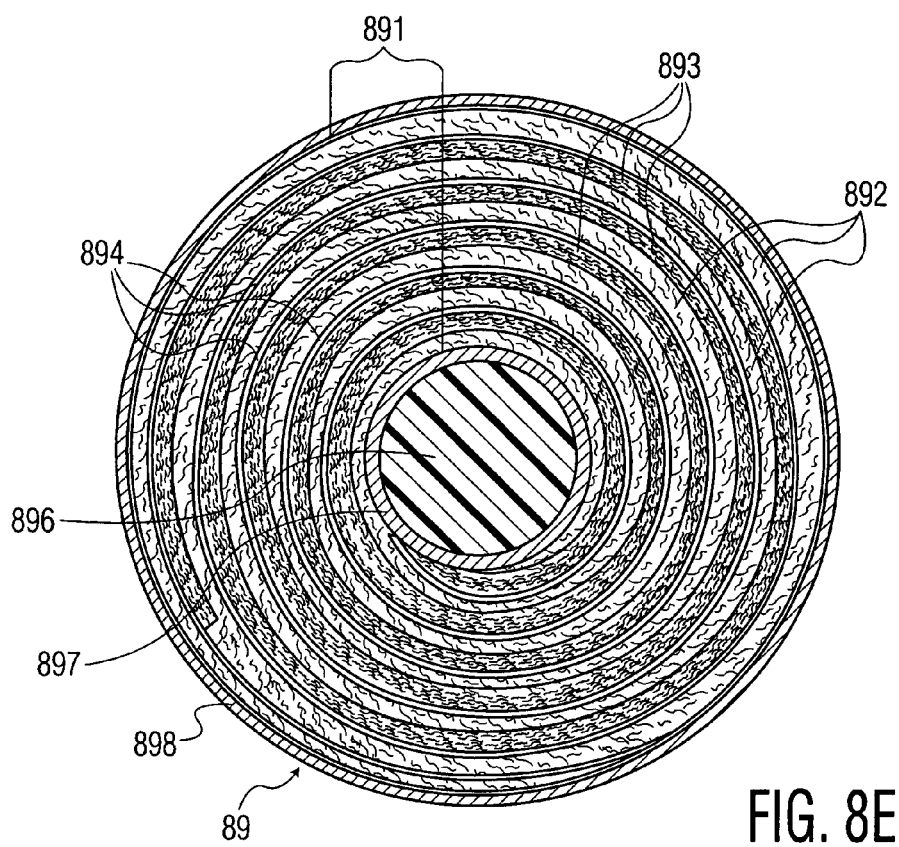
FIG. 8E depicts an end view of a circular filter rolled from filter cloth.
Figure 8F:
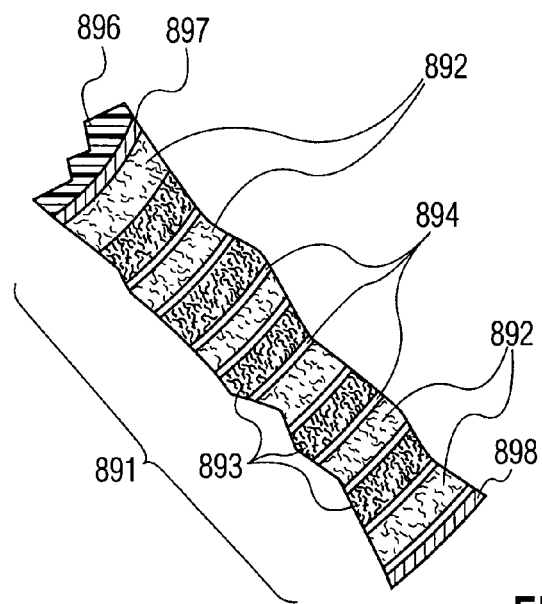
FIG. 8F depicts in cutaway enlargement the roll layers depicted in FIG. 8E.

Because: (A) there are commercially available, relatively flat filter cloths commercially available for the ostomy market; and (B) the present invention substantially eliminates the problem of clogging the filter material, there are additional options for the ostomist made practical by the present invention. (Activated charcoal cloth, cloth having activated charcoal dispersed therein, useable in filtering, and thereby deodorizing, flatus gasses is available from, for example, from Charcoal Cloth International under the brand name Zorflex.) Additional substitutions in the context of FIG. 7, identified below, are now practical and desirable. For example, the use of a filter cloth in a flat filter, and substituting relatively flat, slender, elliptical-profile connector 82 of FIG. 8D for cylindrical connector 62 help to minimize the bulk of the ostomy equipment, a significant concern of many ostomists. The thickness of walls 84 of connector 82 of FIG. 8 is exaggerated somewhat. The discussion of FIG. 9, FIG. 10, FIG. 11, FIG. 11A, FIG. 11B, FIG. 11C, and FIG. 11D expands on aesthetics and additional aspects of the latent tube system, process and tools of the present invention. FIG. 8E, together with further magnified cutaway FIG. 8F, depicts in end view, charcoal cloth 891 having fibers 892 and 893 supported in the wrapping process by gas permeable support 894. Charcoal cloth 891 is wound around thin, circular profile rod 896 having adhesive layer 897 and then wrapped in gas impermeable exterior sheath 898 to form cylindrical filter roll 89. The sheathed filter roll can then be placed in a tube (which can be a tube like connector tube 62 of FIG. 6A, or a tube like latent tube 85 of FIG. 8C). Gas impermeable sheath 898 provides an advantage for latent tube applications by inhibiting radial flow from the filter fibers, thereby accommodating effective filtering even through diametrically loose-fitting filter outer walls, for example, of connector 85, provided the upstream filter end is secured within connector 85 by, e.g., a circumferential elastic band. Charcoal cloth 891 as depicted in filter roll 89 optionally has near its inner core several wraps (or winds) fibers 893 having more charcoal and higher density than immediately adjacent fibers 892. The differential in fiber density facilitates the longitudinal flow of gas through the filter while the gas is nonetheless in close proximity to odor eating charcoal. An alternative would be to use spacing elements interspersed in each wrap of the roll to facilitate gas flow through the filter. The packing density of the filter can be also controlled by the tension on the wind (the tightness of the roll) to provide the appropriately minimal pressure drop, from filter to filter.

Figure 9:
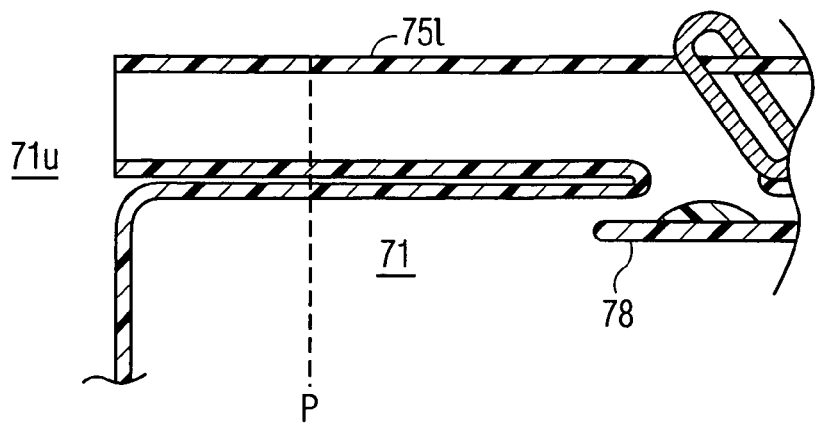
FIG. 9 depicts in partial view cutaway enlargement the upper extremity left side (as depicted) of ostomy bag 71 of FIG. 7.
Figure 10:
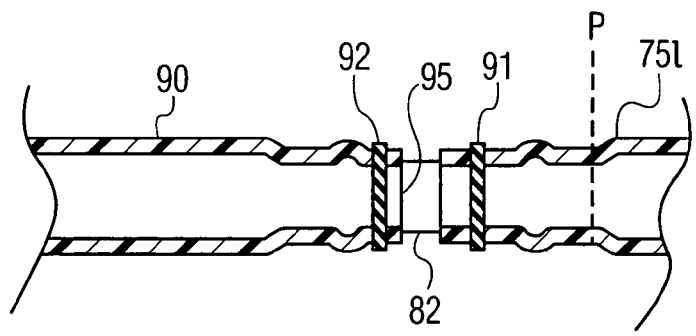
FIG. 10 depicts in frontal perspective partial view a connector linking an ostomy bag versatile tube with a connector to a filter.
Figure 11A:
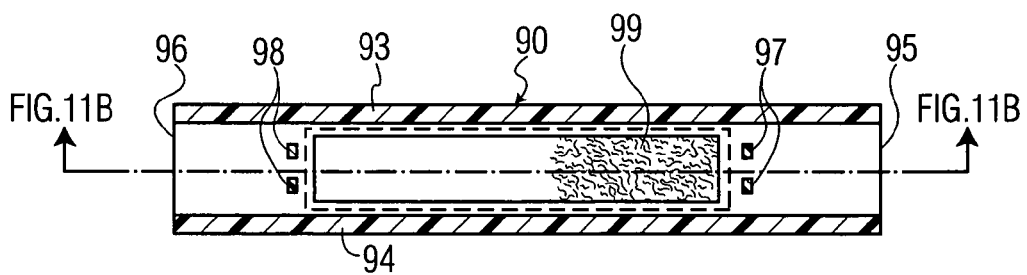
FIG. 11A depicts an enlarged view in partial cutaway of a long thin filter connected as a preferred tool depicted in FIG. 10.
Figure 11B:
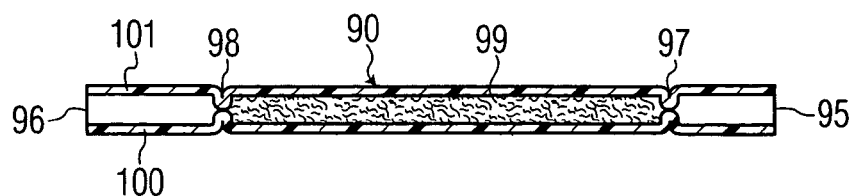
FIG. 11B depicts in cutaway an edge view of the filter depicted in FIG. 11A.

FIG. 9 depicts in enlarged, fragmentary frontal view a portion of the left side of upper extremity 71u of ostomy bag 71 (see FIG. 7). Island baffle 78 minimizes flow of fecal solids into versatile latent tube 75l of ostomy bag 71. FIG. 10 depicts in fragmentary frontal view connector 82 (see FIG. 8D) inserted into versatile tube 75l to a penetration P (dashed line, location also indicated in FIG. 9) and secured by elastic band 91. In accordance with another aspect of this invention, the other end of connector 82 is inserted in filter 90 through filter port 95 and secured in place by elastic band 92. (Connector 62, of FIG. 6A, loaded with, having inserted therein, cylindrical filter roll 89, could substitute for connector 82, but it would add a bulk that could be objectionable to some ostomists.) FIG. 11A depicts in partial cutaway frontal view filter 90 having edge seals 93 and 94 (exaggerated). Filter pad 99 (partially exposed by the cutaway and partially shown in phantom) sandwiched between the front wall 100 and rear wall 101 (see FIG. 11B) of filter 90 and longitudinally located between filter end spot seals 97 and 98 (which assure filter pad 99 does not move longitudinally and also help keep the filter housing from deforming to let unclean gas pass between edge walls and the filter pad). Filter 90 is very flat and unlikely to let much untreated gas pass through without contact with filter pad 99. The fact that filter 90 is comparatively remote in accordance with the present invention also makes it more unlikely for the filter to suffer as significant stress (causing odiferous gas to surge through the filter untreated) as would filters that are directly in or on the ostomy bag main chamber. Even if untreated gas were to pass through one filter the opportunity in accordance with the present invention to have filters connected in series decreases significantly the risk of untreated gas passing through the entire series. Again, the bags and tools of the instant invention provide an added increment of safety and security for the ostomist. Very importantly, it is an issue over which the ostomist has control. That is, if the ostomist's lifestyle, exercise routine or work routine suggests he or she needs a safety margin, more filters could be added. It should be noted, too, that the extra filters do not get wasted. The ostomist can use the entire series until not even the most distal filter has any effectiveness. Alternatively, in privacy the ostomist can break the series connection at any spot to determine which of the first filters are exhausted and replace only those. As depicted in FIG. 10, filter 90 is connected through connector 82 to versatile tube 75. Untreated gas would flow through versatile tube 75 and connector 82 into filter 90 through filter port 95. The structure of filter 90 is depicted in frontal partial cutaway view in FIG. 11A and in edge view cutaway in FIG. 11B (the cutaway along line c—c of FIG. 11A). In some cases it is desirable to have charcoal cloth or other materials packaged within a gas permeable paper to void the mess charcoal can cause. In filter 90 the gas would pass by filter-end spot seals 97 and would then meet and pass in substantial contact with and through long, relatively flat filter pad 99 which is sandwiched between thin frontal plastic layer 100 and thin rear plastic layer 101 (preferably out of the same material that goes into making the ostomy bags and tubes indicated above. The contact with filter pad 99 is intended to deodorize the gas. The gas would eventually flow out port 96 of filter 90, for example to the ostomist's undergarment atmosphere, to another filter as indicated above with reference to FIG. 7, or to another fluid channel, as indicated below with reference to FIG. 13. (Of course, both versatile tube 75 and connector 82 could also contain relatively flat filters made, for example, of charcoal cloth enclosed along their length by a sheath.)

The above-demonstrated flat tube system of filters also accommodates single filters that are longer than depicted in FIG. 11 if commercial demand exists. A number of interrelated factors are considered, for example, in determining the length of the filter and which mechanisms for using the ostomy belt to support the filter. Generally speaking, from the ostomist's perspective, the simpler the system is, the better it is for the ostomist. Longitudinal porosity of the filter pad is a significant factor in determining pad length, as is extent of adhesion, if any, of the filter pad to the walls. (For example, can gas pass along the wall and still be in effective contact with the filter pad?) Filters need to accommodate relatively low-pressure differentials so that the ostomy bag doesn't have to be filled to capacity for sufficient pressure for gaseous release through the filter. Also, having sufficient dwell time of the gas in contact the filter is important so that the gas can interface with and be deodorized by the filter. High porosity and low dwell time requirements for effectiveness at each increment of filter length means the ostomy bag can vent at low pressure, a desirable result, but only if the venting is of deodorized gas. Porosity is controllable by the tightness of the weave of the filter and density of the odor combatant in the weave to accommodate low pressure differentials. Additional filter length (either in a single filter or multiple filters hooked in series) in accordance with the present invention provides another control factor of assistance to the ostomist. Putting a combination of different deodorizing materials in a single filter might be impractical (because the deodorizing materials could interact negatively). However, particularly helpful for such situations in accordance with the instant invention is the use of multiple but different filters in series. For example, the first filter (nearest the bag) could have a porosity value, e.g., of 1.25 cm (0.5 inch) per second at a given pressure, while the second filter might have a porosity value, e.g., of 1.75 cm (0.7 inch) per second, while the third could be even more porous. Such a sequence would help limit impedance of flow while promoting a more uniform dwell time of gas to be treated in each filter. Although that would appear to make life a bit more complicated for the ostomist, appropriate packaging, for example in sets, e.g., labeled by suggested order, could to some extent alleviate ostomists' concern. Another advantage of the present invention is that the latent tube systems facilitate testing of various filters by ostomists themselves to determine which filters best suit the ostomist's needs.

Figure 12A:
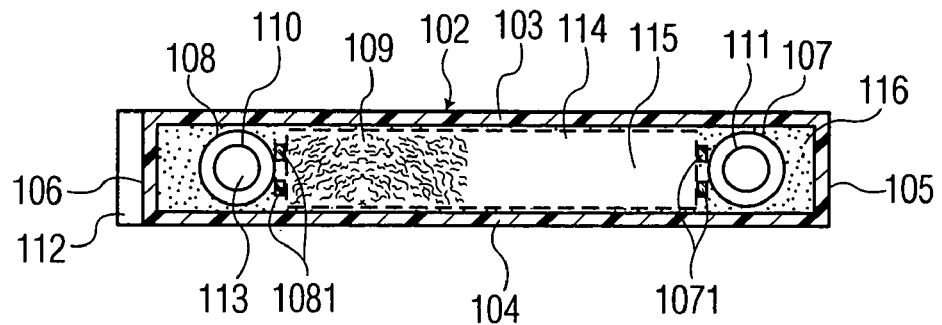
FIG. 12A depicts an enlarged adhesive side view in partial cutaway of another long thin filter as a preferred alternative to the filter depicted in FIG. 6A.
Figure 12B:
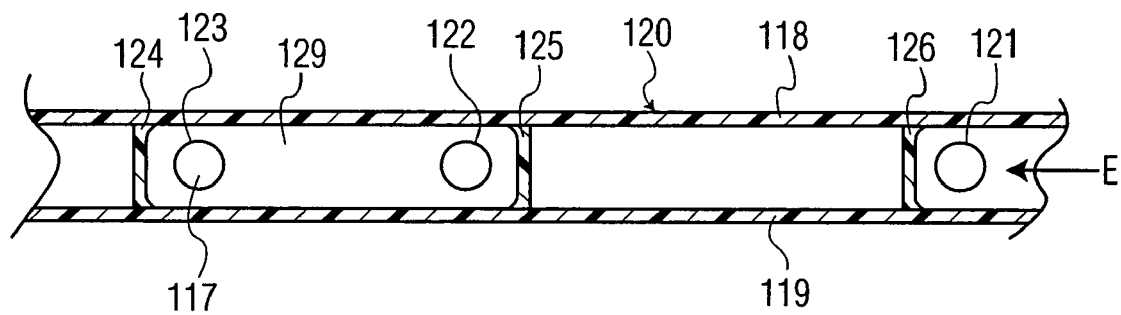
FIG. 12B depicts an enlarged view of a series filter connector latent tube.
Figure 12C:
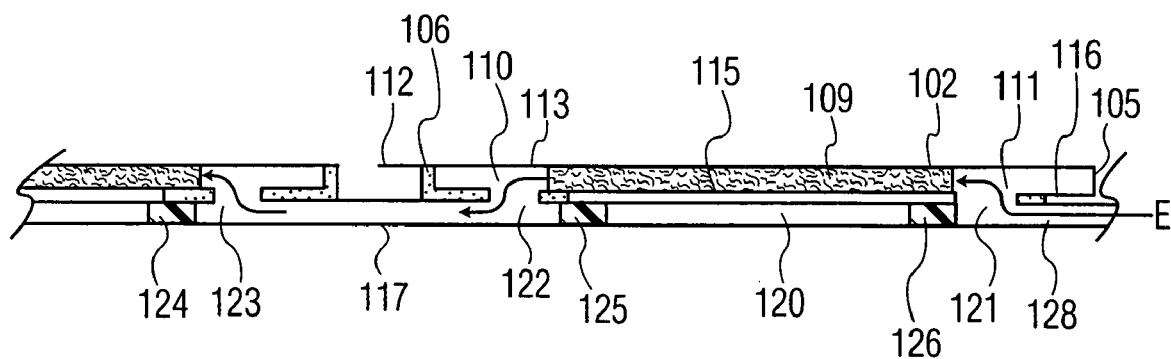
FIG. 12C depicts a substantially enlarged cutaway edge view of filters depicted in FIG. 12A placed adhesive down on the connector latent tube depicted in FIG. 12B.

FIG. 12A depicts in portal side partial cutaway view of adhesive side 116 of filter 102 having portals 110 and 111. Filter 102 has an elongated rectangular filter pad 109 that is sealed between rear wall 113 which is visible through ports 110 and 111 and front wall 114 having an exterior surface having a peripheral area 116 covered by adhesive and a central area 115 free from adhesive. Flatus gas would be deodorized by passing through filter 102, entering at port 111 and exiting at port 110. Both port 110 and 111 are depicted as having reinforced edges 107 and 108 respectively, to better assure port definition integrity. Filter-pad end spotseals 1071 and 1081 which seal rear wall 113 to front wall 114 assure filter 109 does not move longitudinally and also helps keep filter 102 substantially flat during use. (See reference to seals 98 and 97 in reference to FIG. 11A above). Edge seals 103 and 104 are close to filter pad 109 for its full length and therefore provide ample space for gas to pass through filter 102 from port 111 to port 110 in substantial contact with filter pad 109, but very little, if any, space for gas to pass through without having such contact with filter pad 109. End seals 105 and 106 together with side seals 103 and 104 of filter 102 assure that ports 111 and 110 are the only entry and exit routes for gasses. FIG. 12B depicts (with sealed edges 118 and 119 exaggerated) latent filter tube 120 having front wall 129 and rear wall 117 (visible through ports 121, 122, and 123, which ports also optionally have reinforced circumferences to minimize damages to the ports during filter exchange as explained further below). Interval seals 124, 125 and 126, each sealed between walls 117 and 129 and extending from edge seal 118 to edge seal 119, with interval seals 125 and 126 located between ports 122 and 121 thereby preventing gas flow therebetween through tube 120. In use, flatus gas enters filter tube 120 at E in the direction (indicated by the arrow at the right side of FIG. 12B). Interval seal 126 helps guide the gas out port 121 which in proper use would be mated with an intake port of a filter. FIG. 12C depicts latent filter tube 120 of FIG. 12B in mating relationship with filter 102 of FIG. 12A. Filter 102 of FIG. 12A mates when adhesive area 116 of filter 102 is pressed in mating contact with the exterior surface of wall 129 of filter latent tube 120 of FIG. 12B so that ports 110 and 111 of filter 102 mate with filter latent tube 120's ports 122 and 121, respectively; and edges 103 and 104 of filter 102 align with latent tube 120's edges 119 and 118, respectively. Accordingly, as depicted in greatly magnified, side view cutaway in FIG. 12C, when connected from the "E" direction to an ostomy bag (not shown) by one of the connectors depicted and discussed above, latent tube 120 receives flatus gas in receiving chamber 128. The gas would be diverted out of chamber 128 through port 121 of tube 120 and through port 111 into filter 102 where it would begin its path through and beside (in contact with) filter pad 109 of filter 102 in the direction of outlet port 110. Gas reaching the distal end of filter pad 109 would then be forced out of filter 102 through port 110 and through port 122 back into filter tube 120: (a) if additional filters are to be used, for redirection into the next filter (as depicted); or (b) if no other filter is to be used, for release into the environment. Accordingly, filter tube 120 provides the ostomist the further flexibility, again, of using one or a series of filters. Moreover, when one filter becomes exhausted it can be pealed off tube 120 using grip tab 112 of filter 102 for replacement with a new filter, providing a further flexibility advantage.

Figure 13A:
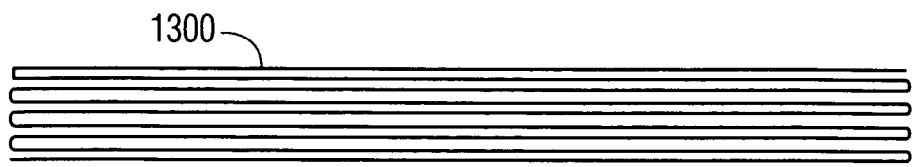
FIG. 13A depicts an exaggerated edge view of a long, folded latent fluid conveyance tube.
Figure 13B:
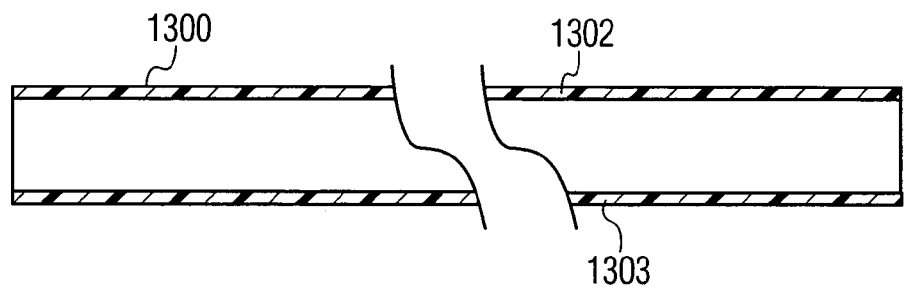
FIG. 13B depicts a flat frontal view of a latent fluid conveyance tube like that of FIG. 12A.

FIG. 13A depicts a side (edge) view of folded latent conveyance tube 1300. The edge of the tube as depicted is approximately the dimension of the edge of an unused but useable ostomy bag having front and rear walls (excluding the mechanism for attachment to the ostomist's body). A preferred conveyance tube of the present invention is made of the same material as an ostomy bag, for example, manufactured by bringing one sheet or strip of material in contact with another and applying heat in a predetermined pattern (in this case to form narrow strips, e.g., directly or by cutting the strips after the sealing is accomplished). The space between the folds is exaggerated so that separate folds could be discerned. One significant advantage of tubes being constructed in this way is that the ostomist is familiar with working with and has confidence in the material. It is liquid and gas impermeable, and importantly, tubes so constructed can easily be squeezed to be free of residual gas. Thus, for example, the tube could be folded and put into the ostomist's pocket or purse (and/or into a small zipper lock type bag) without fear of retaining flatus gas that might otherwise find an embarrassing exit time. A major point of FIG. 13 is to show how easy it can be in accordance with the present invention for an ostomist to carry a conveyance tube (or even several) for his or her convenience, and avoidance of inconvenience to others. The length of latent conveyance tube 1300 as depicted?—longer than a meter (39 inches). How would it be used? In several ways and a few examples undoubtedly will make many more apparent. When riding in a car on a busy expressway with other passengers familiar to the ostomist and his or her ostomy, the bag fills completely (mostly with flatus gas), do you warn everyone that you need to vent and simply open the window and let it go? . . . Or stop, get out and vent? Or, unbutton a couple of buttons on your shirt, unfold your conveyance tube 1300 (which is already connected to a versatile tube of an ostomy bag like that depicted partially in FIG. 6B), put the distal end out a window and then vent? How about when the ostomist is in a hotel room in a big city with his or her spouse? Suppose they are ready to settle down for the evening and suddenly the ostomist finds it necessary to vent before going to bed! Many ventilating systems in home and hotel bathrooms just can't handle the foul odor. Many hotels do not have windows that open. Could the ostomist safely step outside the hotel to vent? A tool in the ostomy system used in conjunction with the latent tube of FIG. 13 solves the problem, and is discussed below. FIG. 13B depicts in frontal fragmented view latent tube 1300 of FIG. 13, with the width and edge seals 1302 and 1303 exaggerated. The length of the tube can vary a great deal. A tube of as short as 20 cm (eight inches) can get the odor outside the ostomist's garments (even in cold climates). A tube of several feet might be necessary to connect with the outside window of the ostomist's bedroom.

Figure 14:
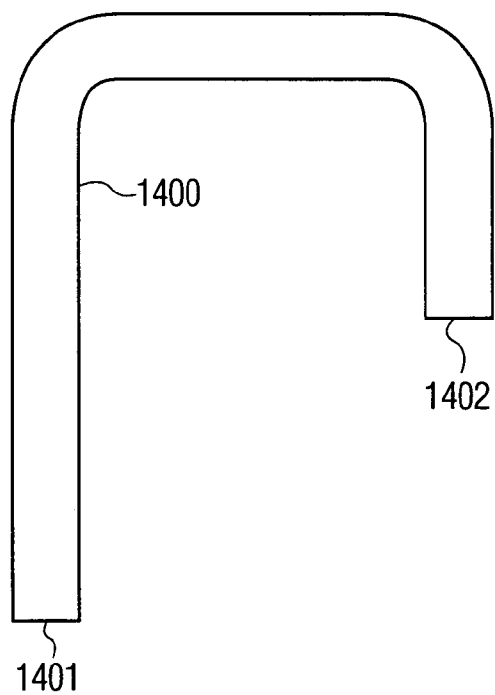
FIG. 14 depicts a formed fluid conveyance tube that is attachable to latent fluid conveyance tubes depicted in FIG. 13A and FIG. 13B.

FIG. 14 depicts in side, fragmented view firm tube 1400 (having ends 1401 and 1402 for use as a tool in conjunction with a fluid conveyance latent tube such as depicted in FIG. 13. The term "firm tube" is intended to include tubes that generally hold their shapes even when not in use. That is, the tube should be tubular even when not in use, but having the tube be somewhat bendable can in some circumstances be helpful. In some circumstances it can be desirable to have a circumferential hump (like hump 67 of connector 62 in FIG. 6A) near end 1401. In the riding in the auto example mentioned above it is helpful to have the distal end of the firm tube tool in a twisted "U" shape to hook on the window and have the open, distal end of the tool hang below and behind (downstream of) the window opening. In the hotel situation mentioned above, there are, for example, at least two ways the instant invention solves the problem. In the first method, using the hotel bathroom sink, the ostomist (a) connects one end of a flexible conveyance latent tube to the distal end of the closed versatile tube of the ostomy bag (using a firm tube connector if necessary) and, the other end of the conveyance tube to the proximal end of the tool (a bendable firm tube) (b) inserts the distal end of the tool (the end closest to the bend in the tool) down the sink drain far enough to reach the curve in the trap, (c) turns the water on fast, and (d) opens the ostomy bag versatile tube and gently applies pressure to the bag to force the gas out. Depending on the sink size and the ostomist's size, the use of a flexible conveyance latent tube of at least about 30 centimeters (one foot) long is desirable. Because the drain may not be clean, the bendable firm tube should be easily cleanable, or be disposable (e.g., a disposable, bendable drinking straw). Ideally, the firm bendable tubes would be longer than some available drinking straws, with a length to the bend of at least 25 cm. (10 in.). The same general procedure can be used to put the gas down the toilet drain. However, a conveyance tube approximately three times the length of the conveyance tube required for gas disposal through the sink could be necessary, depending on the size of the ostomist and the position taken during disposal. The diameter of the firm tube can also vary widely. In each hotel room case mentioned a small diameter tube will likely be useable. In the disposal through the sink a large diameter tube would not be suggested. The non-ostomist might not realize it, but these types of situations are real in the life of an ostomist. The linked series filters and other tools as described herein would make the auto and hotel situations a whole lot more tolerable.

Figure 15:
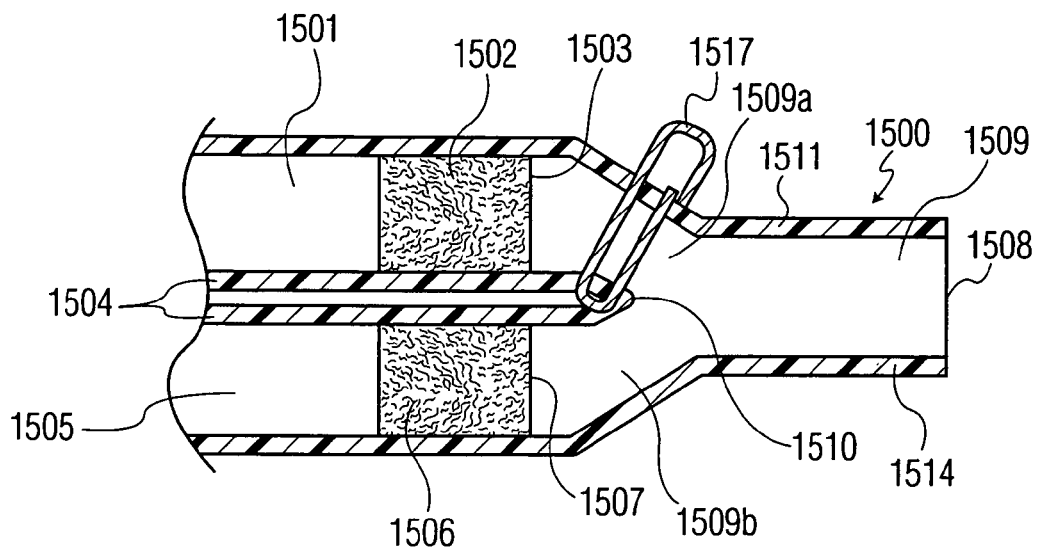
FIG. 15 depicts in cutaway an internal view of a bifurcated latent tube.

FIG. 15 depicts a fragmented frontal partial cutaway "lazy Y" shaped (as depicted) latent bifurcated tube 1500 (which can be constructed in a manner similar to that described for tube 1300 described above). Tube 1500 has: tube end opening 1508 opening to channel 1509 which is separated by dividing seal 1504 (having proximal end 1510) into channels 1509a and 1509b leading respectively to chamber 1501 containing removable filter 1502 having filter end 1503, and chamber 1505 containing removable filter 1506 having filter end 1507. (Advantageously, filters 1502 and 1506 are similar to filter 90 of FIG. 11.) Sealed perimeter edges 1511 and 1514 of channel 1509 are parallel until near the point of furcation leading to channels 1509a and 1509b where seals 1511 and 1514 angle away from each other for a short distance (thus, the "Y shape"), and then perimeter seals 1511 and 1514 turn and again are parallel with each other and parallel to dividing seal 1504. As depicted, channel 1509a leading to chamber 1501 and filter 1502 is temporarily closed by clip 1517, which extends across channel 1509a and part of end 1510 of dividing seal 1504. This filters in parallel arrangement can assist the ostomist (who has confidence in the filters but doesn't know how long a business meeting will last, or how much life one filter has). The ostomist, for example, simply loads one new filter into chamber 1501 and one new filter into chamber 1502. Then the ostomist closes the one of the channels (1509a as depicted) with a simple clip and connects bifurcated tube 1500 to a latent, versatile tube of the ostomy bag the ostomist is wearing according to the present invention. Later on, if the meeting lasts longer than expected, or if the ostomist smells danger, he or she excuses himself or herself for a brief moment, finds a private spot, and removes the clip from the channel leading to the unused filter and places a clip on the channel leading to the used filter and/or on the exit end of the channel housing the used filter.

Figure 16:
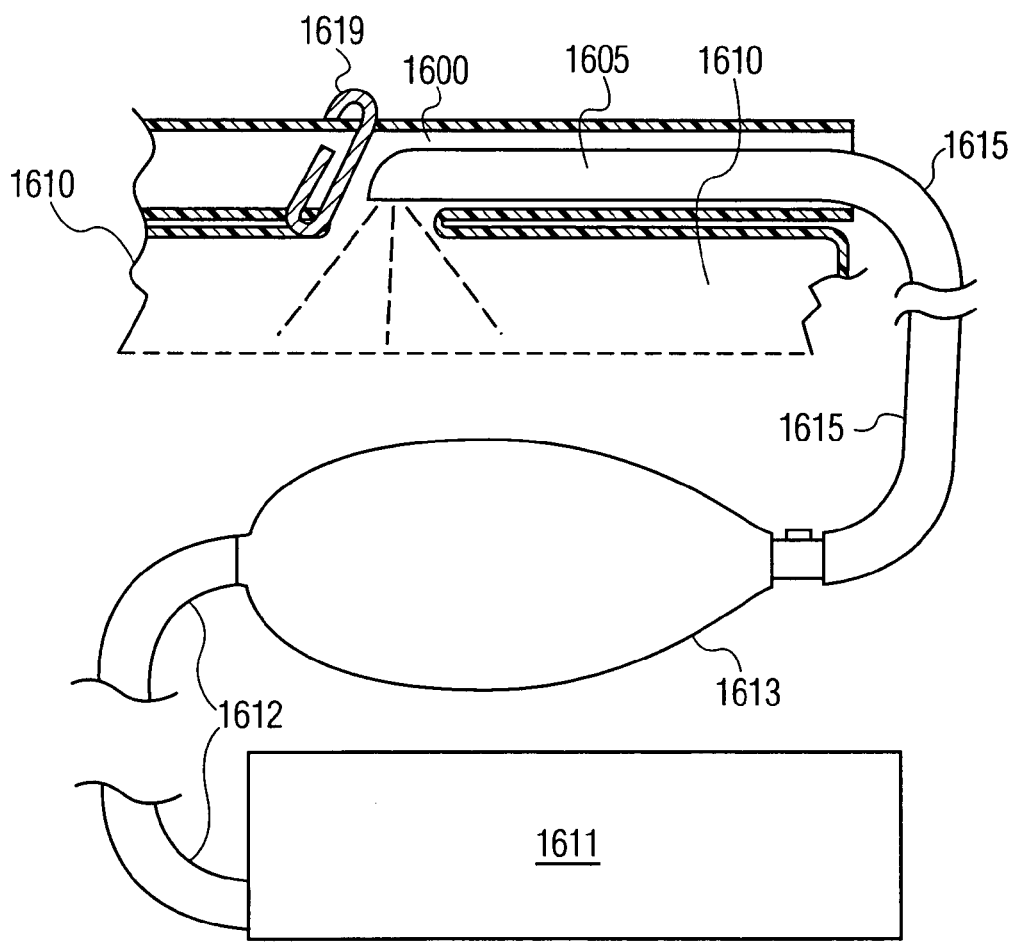
FIG. 16 depicts a portion of an ostomy bag upper extremity with a versatile tube similar to that illustrated in FIG. 7 but having a firm water delivery tube inserted in the versatile tube. The water delivery tube is connected to a water delivery system.

FIG. 16 depicts in fragmentary partial cutaway enlargement view upper extremity right side (plus, as depicted, including a central portion of the left side) of ostomy bag 1610 similar to that depicted as ostomy bag 71 of FIG. 7, with new versatile tube 1600 similar to versatile tube 75r of FIG. 7, with said versatile tube 1600 having inserted therein firm tube 1605 which is connected to a water delivery system for flushing the bag. Partially depicted ostomy bag 1610 is different from ostomy bag 71 as depicted in FIG. 7, for example, in that ostomy bag 1610 optionally has no island baffle, right side versatile tube 1600 is open for fluid communication with the bag main chamber, and left side versatile tube (partially depicted) is temporarily closed by closure means 1619 (whereas in FIG. 7 right side versatile tube 75r was temporarily closed and left side versatile tube 75l was open). If the ostomist wishes to flush after each emptying of the bag, it may be desirable to use a bag without a baffle placed in the way of flow of flushing fluid to get more uniform distribution of the spray. In that event at least one intra-tube baffle such as that depicted in FIG. 1 as baffle 18 may be appropriate for the left side versatile tube, especially if it is used substantially as an open vent with filters. Having a plurality of versatile tubes on a single bag provides the ostomist additional flexibility and convenience. The flushing system can have as its water source any of a variety of mechanisms supplying water through tube 1605. Depicted in FIG. 16 is tube 1605 connected to hose 1615, which in turn is connected to a squeeze bulb pump 1613 drawing water through hose 1612 from reservoir 1611. The washing procedure can be used with a drainable bag and according to the present invention it is simple and relatively free from mess. With ostomy bags and tools according to one aspect of the present invention the ostomist can simply open the bag drainage channel (aimed at an appropriate receptacle, desirably a toilet), move one paper clip, insert a firm flushing tube into a versatile tube of the ostomy bag according to the present invention, place a band around the versatile tube and the firm tube, flush, remove the firm tube, close the drainage channel and replace the paper clip.

Although specific embodiments of the present invention have been described above in detail, it will be understood that this description is merely for purposes of illustration. Various modifications of, and equivalent steps corresponding to, the aspects of the preferred embodiments, in addition to those described above, may be made by those skilled in the art without departing from the spirit of the present invention defined in the following claims, the scope of which is to be accorded the broadest interpretation so as to encompass such modifications and equivalent structures.

What is claimed is:

1. An ostomy bag comprising: (a) a main chamber with an upper extremity having at least one upper extremity seal; and (b) at least one multiple-use latent tube co-formed with said main chamber, said multiple-use latent tube having a proximal end firmly attached to, opening to and capable of fluid communication with said main chamber upper extremity, said latent tube further: (b1) having a defined length to a distal end capable of providing axial gas flow out of said tube; and (b2) as co-formed with said main chamber, having two seals which, except for said attachment, are separated from said upper extremity seal, one latent tube seal proximate to said upper extremity seal of said main chamber and one latent tube seal distal to said main chamber upper extremity seal.

2. An ostomy bag in accordance with claim 1, wherein said main chamber and said latent tube have front-side and body-side walls, and the front-side wall of said main chamber is made of the same kind of material as the front-side wall of said latent tube, and the body-side wall of said main chamber is made of the same kind of material as the body side-wall of said latent tube, and wherein, said proximate latent tube seal as formed is generally equidistant from said upper extremity seal along a substantial part of said length of said proximate latent tube seal.

3. An ostomy bag in accordance with claim 1, in combination with at least one filter in fluid connection with said distal end of said tube, for filtering the gaseous outflow from said ostomy bag.

4. An ostomy bag in accordance with claim 3, wherein a connector is attached in fluid connection by axial insertion into said tube distal end and said filter is connected to said connector.

5. A combination in accordance with claim 3, wherein said filter is also a connector.

6. An ostomy bag in accordance with claim 1, wherein said bag includes a plurality of multiple use latent tubes co-formed with said main chamber, at least two said multiple-use tubes each having a proximal end opening to and capable of fluid communication with said upper main chamber extremity, at least one of said tubes having a distal end capable of providing axial fluid flow out of said tube.

7. An ostomy bag in accordance with claim 6, wherein said bag includes two multiple use tubes co-formed with said main chamber, each of said two tubes having a distal end capable of providing axial fluid flow out of it.

8. An ostomy bag in accordance with claim 6, wherein each of said multiple use tubes is separately closeable near its respective proximal end.

9. An ostomy bag in accordance with claim 1, wherein said main chamber upper extremity has a perimeter edge, and at least said distal end of said latent tube has a perimeter edge that is proximate to and in separable connection with a portion of said main chamber upper extremity edge.

10. An ostomy bag comprising: (A) a main bag chamber having an upper extremity; (B) a multipurpose latent tube co-formed with and external to said main bag chamber, said latent tube having a proximal end attached to and opening to said main bag chamber upper extremity and providing the capability for fluid communication with said upper extremity, said tube also having: (1) a distal end; and (2) significant latent tube length between said proximal end and said distal end, at least a substantial part of said length as co-formed being parallel to and separably attached to said main bag chamber.

11. An ostomy bag in accordance with claim 10, wherein said distal end and said significant latent tube length between said proximal end and said distal end are unattached to said main bag chamber.

12. An ostomy bag in accordance with claim 10, wherein said distal end is capable of providing axial gas flow out of said tube.

13. An ostomy bag in accordance with claim 11, wherein said distal end is capable of providing axial gas flow out of said tube.

14. An ostomy bag in accordance with claim 10, further including a closure means for closing said tube said closure means coformed with said bag.

15. An ostomy bag comprising: (A) a closure means: (B) a main bag chamber having an upper extremity; and (C) a multipurpose latent tube co-formed with said main bag chamber, said latent tube having a proximal end attached to and opening to said main bag chamber upper extremity and providing the capability for fluid communication with said upper extremity, said tube also having: (1) a distal end; and (2) significant latent tube length between said proximal end and said distal end, at least a substantial part of said length as co-formed being parallel to and less than firmly attached to said main bag chamber, wherein said closure means comprises a blank area firmly attached to said main bag chamber proximate said tube proximal end, said blank area having at least one slit therein through which said latent tube can be inserted, wherein said slit is in fluid communication with neither said main bag chamber nor said tube.

16. A stomal waste management system comprising multiple use latent tubing having: (a) front and back walls comprising thin, flexible, water impermeable plastic, said latent tubing further having at least one channel having a flat width dimension no greater than one inch and at least two end openings, at least one of said openings being a proximal end through which gas can enter said tube, which latent tubing takes tubular form as necessary for gas flow therethrough, and wherein said latent tubing has at least one pair of spaced apertures in one of its walls to accommodate attachment of a filter with appropriately mating apertures, said latent tubing further having at least one interval seal between said spaced apertures to route gas out of said tubing and into said filter.

17. A stomal waste management system in accordance with claim 16 wherein said latent tubing has a plurality of: (a) pairs of apertures, and (b) interval seals, to accommodate a plurality of filters.

* * * * *